United States Patent
Miyake et al.

(10) Patent No.: US 10,676,417 B2
(45) Date of Patent: Jun. 9, 2020

(54) METHOD FOR PRODUCING REDUCED HALIDE COMPOUND HAVING UNDERGONE REDUCTION OF CARBON-CARBON UNSATURATED BOND

(71) Applicant: SHIN-ETSU CHEMICAL CO., LTD., Tokyo (JP)

(72) Inventors: Yuki Miyake, Niigata (JP); Takeshi Kinsho, Niigata (JP); Yusuke Nagae, Niigata (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 3 days.

(21) Appl. No.: 16/388,309

(22) Filed: Apr. 18, 2019

(65) Prior Publication Data

US 2019/0322607 A1 Oct. 24, 2019

(30) Foreign Application Priority Data

Apr. 19, 2018 (JP) ................................. 2018-080593

(51) Int. Cl.

| | | |
|---|---|---|
| C07C 41/54 | (2006.01) | |
| B01J 23/80 | (2006.01) | |
| B01J 37/00 | (2006.01) | |
| B01J 37/04 | (2006.01) | |
| B01J 37/08 | (2006.01) | |
| B01J 37/18 | (2006.01) | |
| C07C 17/354 | (2006.01) | |
| C07C 29/17 | (2006.01) | |
| C07C 41/20 | (2006.01) | |
| C07F 7/12 | (2006.01) | |

(52) U.S. Cl.
CPC .............. *C07C 41/54* (2013.01); *B01J 23/80* (2013.01); *B01J 37/009* (2013.01); *B01J 37/04* (2013.01); *B01J 37/08* (2013.01); *B01J 37/18* (2013.01); *C07C 17/354* (2013.01); *C07C 29/172* (2013.01); *C07C 41/20* (2013.01); *C07F 7/127* (2013.01)

(58) Field of Classification Search
None
See application file for complete search history.

(56) References Cited

U.S. PATENT DOCUMENTS 5,808,146 A  9/1998 Goodman et al.

FOREIGN PATENT DOCUMENTS

| CN | 106925332 | 7/2017 |
|---|---|---|
| JP | 2011207901 | 10/2011 |

OTHER PUBLICATIONS

Chelucci, ChemistrySelect 2016, 1, 3699-3704 (Year: 2016).*
European Search Report for Application No. EP-1916-7822 ; dated Aug. 14, 2019. (Year: 2019).*
Brown et al., J. Amer. Chem. Soc. 1963, 86:1005-1006. (Year: 1963).*
Apparu et al. "Méthode de synthèse d'acides gras marquès substitués ou non en alpha et en beta", Bull. Soc. Chim. Fr. 1:118-124 (1988).
Chelucci "One-pot Hydrodehalogenation-Hydrogenation of Alkenyl Bromides with Nickel Boride: an Essay Access to Di- and Trisubstituted Ethanes from Aldehydes", ChemistrySelect 1:3699-3704 (2016)
Guiard et al. "Gram Scale-up Synthesis of all-(Z)-Cyclododecatetraene: A Comparison between Intramolecular Wittng and Ring Closing Metathesis Approaches", Synlett 4:553-556 (2001).
Khurana et al. "Facile reductive dehalogenation of organic halides with nickel boride at ambient temperature", Can. J. Chem., 86:1052-1054 (2008).
Sarma et al. "Dehalogenation of Alpha-Haloketones and Vic-Dibromides", Tetrahedron Letters 26(38):4657-4660.
Van et al. "Female Sex Pheromones of Two Japanese Saturniid Species, *Rhodinia fugax* and *Loepa sakaei*: Identification, Synthesis, and Field Evaluation", J Chem Ecol 41:1-8 (2015).
Acosta et al. "Ttansition metals as dopants on nickel borides: Their catalytic activity effect on hydrogenation reactions", Catalysis Today 133-135:49-55 (2008).
Extended European Search Report corresponding to European Application No. 19167822.6 dated Aug. 21, 2019.

* cited by examiner

*Primary Examiner* — Clinton A Brooks
*Assistant Examiner* — Kofi Adzamli
(74) *Attorney, Agent, or Firm* — Myers Bigel, P.A.

(57) ABSTRACT

A halide compound having one or more carbon-carbon unsaturated bonds is catalytically reduced with substantially no dehalogenation to produce a reduced halide compound in which at least one of the one or more unsaturated bonds is reduced. Specifically provided is a method for producing a reduced halide compound including steps of: reacting a nickel compound, a zinc compound, and a borohydride compound in a solvent to obtain a reduction catalyst; and subjecting a halide compound having one or more carbon-carbon unsaturated bonds to catalytic reduction in the presence of the reduction catalyst to reduce at least one of the one or more carbon-carbon unsaturated bonds to thereby obtain a reduced halide compound.

7 Claims, No Drawings

METHOD FOR PRODUCING REDUCED HALIDE COMPOUND HAVING UNDERGONE REDUCTION OF CARBON-CARBON UNSATURATED BOND

RELATED APPLICATION

This application claims priority from Japanese Patent Application No. 2018-080593, filed Apr. 19, 2018, the disclosures of which is incorporated by reference herein in its entirety.

FIELD OF THE INVENTION

The invention relates to a method for producing a reduced halide compound having undergone reduction of at least one carbon-carbon unsaturated bond by catalytic reduction (hydrogenation).

BACKGROUND OF THE INVENTION

Catalytic reduction of reducing a carbon-carbon unsaturated bond, that is, a carbon-carbon triple bond (C≡C) or a carbon-carbon double bond (C=C), into a carbon-carbon saturated bond (C—C) achieves high production efficiency, uses hydrogen as a clean reagent, gives a few waste products, and thus is widely used in industries. For example, in the production of margarine, a nickel salt supported on purified diatomaceous earth is dry-reduced, dispersed in a hardened oil, and solidified, and the resulting nickel catalyst is used for the catalytic reduction. In the production of agrochemicals or drugs, a palladium catalyst such as Lindlar catalyst is used for the catalytic reduction.

However, when a compound having a halogen atom in the molecule is subjected to catalytic reduction using a nickel boride catalyst without a catalyst poison or using a palladium catalyst, dehalogenation simultaneously occurs unfortunately (G. Chelucci et al., ChemistrySelect, 2016, 1, 3699-3704; B. Nand et al., Can. J. Chem., 2008, 86, 1052-1054; and R. P. Sharma et al., Tetrahedron Letters, 1985, 26 (38), 4657-4660).

Accordingly, there have been reported, for example, a method of using a platinum catalyst such as platinum oxide (Marcel Apparu et al., Bull. Soc. Chim. Fr., 1988, 1, 118-124), a method of using a Raney nickel catalyst (JP 2011-207901A), and a method of using a nickel boride catalyst together with a catalyst poison for reducing the activity (Jean-Luc Parrain et al., Synlett, 2001, 4, 553-556; and Takashi Miyachi et al., J. Chem. Ecol., 2015, 41, 1-8).

SUMMARY OF THE INVENTION

However, the platinum catalyst in the method by Marcel Apparu et al. is expensive, and thus is not economical from the viewpoint of industrial production. The Raney nickel catalyst used in JP 2011-207901A is not an inexpensive reagent, is ignitable when dried, and thus is difficult to use industrially from the viewpoint of safety.

In the method by Jean-Luc Parrain et al. and the method by Takashi Miyachi et al., a catalyst poison is used to lower the activity of a nickel boride catalyst, and thus a carbon-carbon triple bond (C≡C) is not reduced into a carbon-carbon single bond (C—C), but a carbon-carbon double bond (C=C) remains.

An object of the invention is to subject a halide compound having one or more carbon-carbon unsaturated bonds to catalytic reduction with substantially no dehalogenation to reduce at least one of the one or more carbon-carbon unsaturated bonds to obtain a reduced halide compound.

As a result of intensive studies, the inventors have found that a catalyst prepared by reacting a nickel compound, a zinc compound and a borohydride compound in a solvent enables catalytic reduction to be carried out with substantially no dehalogenation, and have completed the present invention.

In an aspect of the invention, there is provided a method for producing a reduced halide compound, comprising steps of:

reacting a nickel compound, a zinc compound, and a borohydride compound in a solvent to obtain a reduction catalyst, and subjecting a halide compound having one or more carbon-carbon unsaturated bonds to catalytic reduction in the presence of the reduction catalyst to reduce at least one of the one or more carbon-carbon unsaturated bonds to thereby obtain a reduced halide compound.

In another aspect of the invention, there is provided a reduction catalyst for reducing a carbon-carbon unsaturated bond of a halide compound, the reduction catalyst being prepared by reacting a nickel compound, a zinc compound, and a borohydride compound in a solvent.

In still another aspect of the invention, there is provided a catalytic reduction method for a halide compound having one or more carbon-carbon unsaturated bonds, comprising a step of subjecting said halide compound to catalytic reduction in the presence of a catalyst which is prepared by reacting a nickel compound, a zinc compound, and a borohydride compound in a solvent, to obtained a reduced halide compound in which at least one of the one or more carbon-carbon unsaturated bonds is reduced.

According to the invention, a halide compound having one or more carbon-carbon unsaturated bonds can be catalytically reduced with substantially no dehalogenation, so that a reduced halide compound in which at least one of the one or more carbon-carbon unsaturated bonds is reduced can be produced economically and safely at a high yield.

DETAILED DESCRIPTION OF THE PREFERRED EMBODIMENTS

A reduction catalyst which is prepared by reacting a nickel compound, a zinc compound, and a borohydride compound in a solvent and which reduces a halide compound having one or more carbon-carbon unsaturated bonds to obtain a reduced halide compound in which at least one of the one or more carbon-carbon unsaturated bonds is reduced, is hereinafter also called "NiZn catalyst". In other words, the NiZn catalyst is prepared by reacting a nickel compound, a zinc compound, and a borohydride compound in a solvent.

The nickel compound is preferably a nickelous (i.e. divalent nickel) compound from the viewpoint of handleability. Examples of the nickelous compound include a nickelous salt.

Examples of the nickelous salt include a nickelous halide such as nickel(II) chloride, nickel(II) bromide and nickel(II) iodide; nickel(II) acetate; and nickel(II) carbonate. Nickel(II) chloride or nickel(II) acetate is preferred from the viewpoint of handleability. The nickel compound may be an anhydride or a hydrate. The nickel compound may be used optionally in combination of two or more nickel compounds. A commercially available nickel compound may be used.

The amount of the nickel compound is preferably 0.0005 to 0.200 mol and more preferably 0.002 to 0.100 mol relative to 1 mol of the halide compound having at least one carbon-carbon unsaturated bond from the viewpoint of the activity of the NiZn catalyst.

The zinc compound is preferably a divalent zinc compound from the viewpoint of handleability. Examples of the divalent zinc compound include a divalent zinc salt.

Examples of the zinc salt include a zinc halide such as zinc(II) chloride, zinc(II) bromide and zinc(II) iodide; zinc (II) acetate; zinc(II) oxide; zinc(II) sulfate; and zinc(II) carbonate. Zinc(II) oxide or zinc(II) acetate is preferred from the viewpoint of handleability. The zinc compound may be used optionally in combination of two or more zinc compounds. A commercially available zinc compound may be used.

The amount of the zinc compound is preferably 0.001 to 0.100 mol and more preferably 0.005 to 0.050 mol relative to 1 mol of the halide compound having at least one carbon-carbon unsaturated bond from the viewpoint of the activity of the NiZn catalyst.

The molar ratio of the zinc compound to the nickel compound is preferably 0.1 to 4.0, more preferably 0.4 to 2.0, and even more preferably 0.5 to 1.5 from the viewpoint of the activity of the NiZn catalyst.

Examples of the borohydride compound include an alkali metal borohydride such as lithium borohydride, sodium borohydride and potassium borohydride; an alkaline earth metal borohydride such as magnesium borohydride and calcium borohydride; an alkali metal cyanoborohydride such as lithium cyanoborohydride, sodium cyanoborohydride and potassium cyanoborohydride; and an alkaline earth metal cyanoborohydride such as magnesium cyanoborohydride and calcium cyanoborohydride. Sodium borohydride is preferred from the viewpoint of economy. The borohydride compound may be used optionally in combination of two or more borohydride compounds. A commercially available borohydride compound may be used.

The amount of the borohydride compound is preferably 0.001 to 0.150 mol and more preferably 0.005 to 0.070 mol relative to 1 mol of the halide compound having at least one carbon-carbon unsaturated bond from the viewpoint of the activity of the NiZn catalyst.

The molar ratio of the borohydride compound to the nickel compound is preferably 1.0 to 5.0, more preferably 1.0 to 2.0, and even more preferably 1.0 to 1.5 from the viewpoint of the activity of the NiZn catalyst.

The nickel compound, the zinc compound and the borohydride compound may be reacted in a solvent to obtain a NiZn catalyst. Examples of the particularly preferred combination of the nickel compound, the zinc compound and the borohydride compound include a combination of nickel(II) acetate, zinc(II) oxide and sodium borohydride, a combination of nickel(II) acetate, zinc(II) acetate and sodium borohydride, and a combination of nickel(II) chloride, zinc(II) oxide and sodium borohydride. A combination of nickel(II) acetate, zinc(II) oxide and sodium borohydride is more preferred from the viewpoint of economy.

Examples of the solvent include an alcohol, a hydrocarbon, an ether, and a aprotic polar solvent.

Examples of the alcohol include a linear saturated alcohol having 1 to 10 carbon atoms, such as methanol, ethanol, 1-propanol, 1-butanol, 1-pentanol, 1-hexanol, 1-heptanol, 1-octanol, 1-nonanol and 1-decanol; and a branched saturated alcohol having 3 to 10 carbon atoms, such as 2-propanol, 2-butanol, 2-pentanol, 2-hexanol, 2-heptanol, 2-octanol, 2-nonanol and 2-decanol.

Examples of the hydrocarbon include hexane, heptane, benzene, toluene, xylene and cumene.

Examples of the ether include diethyl ether, dibutyl ether, diethylene glycol diethyl ether, diethylene glycol dimethyl ether, tetrahydrofuran, 4-methyltetrahydropyran, 1,4-dioxane, and ethylene glycol dimethyl ether.

Examples of the aprotic polar solvent include N,N-dimethylformamide, N,N-dimethylacetamide, acetonitrile, dichloromethane, chloroform, and trichloroethylene.

The solvent is preferably an alcohol from the viewpoint of reactivity, and is more preferably methanol, ethanol or 2-propanol. The solvent may be used optionally in combination of two or more solvents. A commercially available solvent may be used.

When a halide compound having a carbon-carbon unsaturated bond has a formyl group protected by a protective group to form O,O-acetal, or has an ester group, an alcohol solvent corresponding to the acetal structure or the ester structure is preferably used to prepare the NiZn catalyst in order to avoid transacetalization or transesterification which makes a reaction system complicated.

The amount of the solvent is preferably 1 to 3,000 g and more preferably 20 to 800 g relative to 1 mol of the halide compound having at least one carbon-carbon unsaturated bond from the viewpoint of reactivity. The molar ratio of the solvent to the nickel compound is preferably 10 to 1,000, more preferably 50 to 300, and even more preferably 100 to 200 from the viewpoint of the activity of the NiZn catalyst.

The reaction temperature for preparing the NiZn catalyst is preferably 10 to 100° C. and more preferably 20 to 70° C. from the viewpoint of the activity of the NiZn catalyst.

The reaction time for preparing the NiZn catalyst varies depending on reaction scales and may be 0.5 to 24 hours from the viewpoint of productivity.

The NiZn catalyst prepared in the above manner is supposed to have a different structure from that of a P-2Ni catalyst, which is prepared by reacting a nickel compound with sodium borohydride in a solvent. The P-2Ni catalyst is a viscous liquid catalyst in which pieces of the catalyst gather together by weak interactions to form large lumpy particles, whereas the NiZn catalyst is a smoothly flowing liquid catalyst in which pieces of the catalyst are supposed to have further weaker interactions therebetween.

According to the invention, there is provided a method for producing a reduced halide compound, comprising a step of subjecting a halide compound having one or more carbon-carbon unsaturated bonds to catalytic reduction in the presence of the NiZn catalyst to reduce at least one of the one or more carbon-carbon unsaturated bonds to thereby obtain a reduced halide compound.

Although the halide compound having at least one carbon-carbon unsaturated bond may contain double bonds of an aromatic ring, the double bonds of an aromatic ring are not reduced by catalytic reduction, but a least one double or triple bond other than the double bonds of an aromatic ring is reduced by catalytic reduction. As a result, at least one of the one or more carbon-carbon unsaturated bonds is reduced. Thus, an at least partially reduced halide compound is obtained. When a halide compound having at least one carbon-carbon unsaturated bond contains no double bonds of an aromatic ring but contains one or more double and/or triple bonds other than the double bonds of an aromatic ring, control of reaction conditions including a reaction temperature of the catalytic reduction enables selective reduction of at least one highly reactive unsaturated bond of the one or more double and/or triple bonds, or enables reduction of all of the one or more double and/or triple bonds. As a result, at least one of the one or more carbon-carbon unsaturated bonds is reduced. Thus, an at least partially reduced halide compound is obtained. In other words, the halide compound having at least one carbon-carbon unsaturated bond to be subjected to catalytic reduction is a halide compound having one or more double and/or triple bonds other than the double bonds of an aromatic ring and having optional double bonds of an aromatic ring. The halide compound having undergone reduction of at least one of one or more carbon-carbon unsaturated bonds by catalytic reduction is a halide compound in which at least one of the one or more double and/or triple bonds other than the double bonds of an aromatic ring has been catalytically reduced without dehalogenation.

The catalytic reduction may be carried out in situ by adding a halide compound having at least one carbon-carbon unsaturated bond into a system in which a NiZn catalyst has been prepared, or may be carried out separately in such a manner that a NiZn catalyst is prepared and then a required amount of the NiZn catalyst is taken out therefrom and is added to a halide compound having at least one carbon-carbon unsaturated bond. The catalytic reduction in situ, in which a halide compound having at least one carbon-carbon unsaturated bond is added into a system in which a NiZn catalyst has been prepared, is preferable from the viewpoint of the simple catalytic reduction.

Next, the method for producing a reduced halide compound in which at least one of one or more carbon-carbon unsaturated bonds of a halide compound is reduced will be described, by referring, as an example, to a step of subjecting a halide compound of General Formula (1) having one or more carbon-carbon unsaturated bonds to catalytic reduction in the presence of a NiZn catalyst to obtain a reduced halide compound of General Formula (2) in which at least one of the one or more carbon-carbon unsaturated bonds is reduced.

such as a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group and an n-octadecyl group; a branched saturated hydrocarbon group such as an isopropyl group, a 1-methylpropyl group, a 2-methylpropyl group, a 2,2-dimethylpropyl group, a 2-methylbutyl group and a tert-butyl group; a linear unsaturated hydrocarbon group such as a 2-propenyl group, a 2-butenyl group, a 2-pentenyl group, a 2-hexenyl group, a 2-heptenyl group, a 2-octenyl group, a 2-nonenyl group, a 2-propynyl group, a (2E)-2-hexenyl group, a 2,5-hexadienyl group, a 3,6-heptadienyl group, a 3,6-nonadienyl group, a 2,5,8-decatrienyl group, a 3,6,9-undecatrienyl group and a 3,6,9,12,15-octadecapentaenyl group; a branched unsaturated hydrocarbon group such as a 2-methyl-2-propenyl group; a cyclic saturated hydrocarbon group such as a cyclopropyl group, a 2-methylcyclopropyl group, a cyclobutyl group, a cyclopentyl group, a cyclohexyl group, a cycloheptyl group and a cyclooctyl group; an aryl group such as a phenyl group, a naphthyl group, an anthryl group, a phenanthryl group and a biphenyl group; and an aralkyl group such as a benzyl group, a 1-phenethyl group, a 2-phenethyl group, a 3-phenylpropyl group, a 2-phenylpropyl group and a 1-phenylpropyl group.

Examples of the acyl group of $R^1$, $R^2$, $R^3$ and $R^4$ include an acetyl group, a propanoyl group, a butanoyl group, a pentanoyl group and a hexanoyl group.

Examples of the divalent hydrocarbon group of $R^1$-$R^2$, $R^1$-$R^3$, $R^1$-$R^4$, $R^2$-$R^3$, $R^2$-$R^4$ and $R^3$-$R^4$ include a linear saturated hydrocarbon group such as a methylene group, an

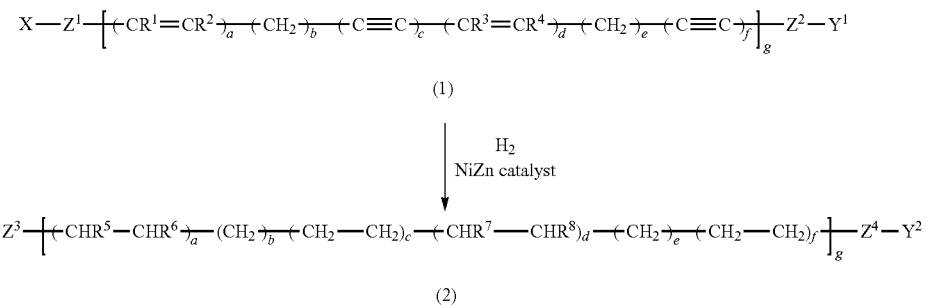

In General Formula (1), X is a halogen atom. Examples of the halogen atom include a fluorine atom, a chlorine atom, a bromine atom, and an iodine atom. A chlorine atom, a bromine atom, or an iodine atom is preferred from the viewpoint of handleability or ease in preparation of a halide.

In General Formula (1), $R^1$, $R^2$, $R^3$ and $R^4$ are each independently a hydrogen atom, a halogen atom, a monovalent hydrocarbon group having 1 to 18 carbon atoms (preferably having 1 to 6 carbon atoms), or an acyl group having 1 to 18 carbon atoms (preferably having 1 to 6 carbon atoms) beside the carbon atom of a carbonyl group; or are bonded together to form a divalent hydrocarbon group, $R^1$-$R^2$, $R^1$-$R^3$, $R^1$-$R^4$, $R^2$-$R^3$, $R^2$-$R^4$, or $R^3$-$R^4$, having 1 to 18 carbon atoms, preferably having 1 to 6 carbon atoms.

Examples of the halogen atom of $R^1$, $R^2$, $R^3$ or $R^4$ are the same as those of X in General Formula (1).

Examples of the monovalent hydrocarbon group of $R^1$, $R^2$, $R^3$, and $R^4$ include a linear saturated hydrocarbon group ethylene group, a 1,3-propylene group, a 1,4-butylene group, a 1,1-pentylene group, a 1,5-pentylene group, a 1,6-hexylene group, a 1,7-heptylene group, a 1,8-octylene group, a 1,9-nonylene group, a 1,10-decylene group, a 1,11-undecylene group, a 1,12-dodecylene group, a 1,13-tridecylene group and a 1,14-tetradecylene group; a branched saturated hydrocarbon group such as a 1,2-propylene group, a 2-methyl-1,3-propylene group, a 2,2-dimethyl-1,3-propylene group, a 1,2-butylene group, a 1,3-butylene group, a 2-isopropyl-1,4-butylene group, a 1,4-pentylene group, a 2,3-dimethyl-2,3-butylene group, a 3-methyl-1,5-pentylene group and a 2-methyl-1,6-hexylene group; a linear unsaturated hydrocarbon group such as a vinylene group, a 1-vinylethylene group, a (Z)-2-butene-1,4-diyl group, a 1,4-butynylene group, 1,5-pentenylene group, a 1,6-hexenylene group, a 1,7-heptenylen group, a 1,8-octenylene group, a 1,9-nonenylen group, a 1,6-hexadienylene group, a 1,7-heptadienylene group, a 1,9-nonadienylene group, a 1,9- nonatrienylene group, a 1,11-undecatrienylen group and a 1,16-hexadecatetraenylen group; a branched unsaturated hydrocarbon group such as a 2-methylene-1,3-propylene group; and a cyclic hydrocarbon group such as a 1,2-cyclopropylene group, a 1,2-cyclobutylene group, a 1,2-cyclopentylene group, a 1,2-cyclohexylene group, a 1,2-cycloheptylene group, a 1,2-cyclooctylene group, a 1,2-phenylene group, a 1,3-phenylene group, a 1,4-phenylene group, a 1,2-naphthylene group, a 1,4-dimethylbenzene-7,8-diyl group, a benzylene group, a 1-phenethylene group, a 1-phenylpropylene group, a naphthylene group, an anthrylene group, a phenanthrylene group and a biphenylene group.

In addition to the above examples of the monovalent or divalent hydrocarbon group, hydrocarbon groups which are regioisomeric, stereoisomeric or geometrically isomeric to the above examples may be used.

At least one of the hydrogen atoms of such a monovalent or divalent hydrocarbon group may be substituted by an alkyl group having 1 to 4 carbon atoms, such as a methyl group, an ethyl group, an isopropyl group, a butyl group, an isobutyl group, a sec-butyl group and a tert-butyl group; an alkenyl group such as a 3-butenyl group; an aryl group having 6 or 7 carbon atoms, such as a phenyl group, an o-tolyl group, a m-tolyl group and a p-tolyl group; an aralkyl group having 7 to 8 carbon atoms, such as a benzyl group, a 4-methylbenzyl group and a 4-methoxybenzyl group; a trialkylsilyl group such as a trimethylsilyl group; a halogen atom such as a chlorine atom, a bromine atom, an iodine atom and a fluorine atom; an alkoxy group such as a methoxy group and an ethoxy group; a nitro group; a cyano group; or the like.

$Z^1$ and $Z^2$ are each independently a divalent hydrocarbon group having 1 to 18 carbon atoms, preferably having 1 to 8 carbon atoms, or a single bond.

Examples of the divalent hydrocarbon group of $Z^1$ and $Z^2$ include a methylene group and examples of the divalent hydrocarbon group of $R^1$, $R^2$, $R^3$ and $R^4$ in General Formula (1).

$Y^1$ in General Formula (1) is a hydrogen atom, a halogen atom, a protected formyl group, a hydroxy group, an acyloxy group, an alkoxy group, an alkoxyalkoxy group, a carboxy group, an amino group, an amino group monosubstituted with a monovalent hydrocarbon group having 1 to 18 carbon atoms, an amino group disubstituted with two monovalent hydrocarbon groups each having 1 to 18 carbon atoms, an acylamino group, a silyl group, or an alkoxycarbonyloxy group.

Examples of the halogen atom of $Y^1$ are the same as those of the halogen atom of X in General Formula (1).

Examples of the protected formyl group of $Y^1$ include a formyl group protected by a protective group to form O,O-acetal, a formyl group protected by a protective group to form S,S-acetal (thioacetal), a formyl group protected by a protective group to form N,O-acetal, and a formyl group protected by a protective group to form N,N-acetal. A formyl group protected by a protective group to form O,O-acetal is preferred from the viewpoint of versatility.

$Y^1$, which is the formyl group protected by a protective group to form O,O-acetal, is expressed by —CHOR$^9$(OR$^{10}$) as General Formula (3). In General Formula (3), $R^9$ and $R^{10}$ are each independently a monovalent hydrocarbon group having 1 to 18 carbon atoms, preferably having 1 to 6 carbon atoms, or are bonded together to form a divalent hydrocarbon group, as $R^9$-$R^{10}$, having 1 to 18 atoms, preferably having 2 to 6 carbon atoms. Examples of the monovalent hydrocarbon group and the divalent hydrocarbon group include examples of the monovalent hydrocarbon group and the divalent hydrocarbon group of $R^1$, $R^2$, $R^3$ and $R^4$ in General Formula (1).

Considering reactivity in deprotection, ease in purification, and/or availability, the divalent hydrocarbon group of $R^9$-$R^{10}$ is preferably a lower divalent hydrocarbon group (preferably having 2 to 6 carbon atoms) because the reactivity is high, and by-products generated by deprotection can be easily removed by water washing or concentration. Considering the above, particularly preferred examples of the divalent hydrocarbon group of $R^9$-$R^{10}$ include an ethylene group, a 1,2-propylene group, a 1,3-propylene group, a 1,2-butylene group, a 1,3-butylene group, a 2,3-dimethyl-2,3-butylene group, a 1,5-pentylene group, and a 1,6-hexylene group.

$Y^1$, which is the formyl group protected by a protective group to form S,S-acetal (thioacetal), is expressed by —CHSR$^{11}$(SR$^{12}$). In this formula, $R^{11}$ and $R^{12}$ are each independently a monovalent hydrocarbon group preferably having 1 to 18 carbon atoms, more preferably having 1 to 6 carbon atoms, or an acyl group preferably having 1 to 18 carbon atoms (more preferably having 1 to 6 carbon atoms) beside the carbon atom of a carbonyl group, or are bonded together to form a divalent hydrocarbon group, $R^{11}$-$R^{12}$, preferably having 1 to 18 carbon atoms, more preferably having 2 to 6 carbon atoms. Examples of the monovalent hydrocarbon group, the acyl group and the divalent hydrocarbon group include examples of the monovalent hydrocarbon group, the acyl group and the divalent hydrocarbon group of $R^1$, $R^2$, $R^3$ and $R^4$ in General Formula (1).

$Y^1$, which is the formyl group protected by a protective group to form N,O-acetal, is expressed by —CH(NR$^{13}$R$^{14}$)(OR$^{15}$). In this formula, $R^{13}$ is a hydrogen atom, a monovalent hydrocarbon group preferably having 1 to 18 carbon atoms, more preferably having 1 to 6 carbon atoms, or an acyl group preferably having 1 to 18 carbon atoms (more preferably having 1 to 6 carbon atoms) beside the carbon atom of a carbonyl group. $R^{14}$ is a monovalent hydrocarbon group preferably having 1 to 18 carbon atoms, more preferably having 1 to 6 carbon atoms, or an acyl group preferably having 1 to 18 carbon atoms (more preferably having 1 to 6 carbon atoms) beside the carbon atom of a carbonyl group. $R^{15}$ is a monovalent hydrocarbon group preferably having 1 to 18 carbon atoms, more preferably having 1 to 6 carbon atoms, or is bonded to $R^{14}$ to form a divalent hydrocarbon group, $R^{14}$-$R^{15}$, preferably having 1 to 18 carbon atoms, more preferably having 2 to 6 carbon atoms. Examples of the monovalent hydrocarbon group, the acyl group and the divalent hydrocarbon group include examples of the monovalent hydrocarbon group, the acyl group and the divalent hydrocarbon group of $R^1$, $R^2$, $R^3$ and $R^4$ in General Formula (1).

$Y^1$, which is the formyl group protected by a protective group to form N,N-acetal, is expressed by —CH(NR$^{16}$R$^{17}$)(NR$^{18}$R$^{19}$). In this formula, $R^{16}$ and $R^{18}$ are each independently a hydrogen atom, a monovalent hydrocarbon group preferably having 1 to 18 carbon atoms, more preferably having 1 to 6 carbon atoms, or an acyl group preferably having 1 to 18 carbon atoms (more preferably having 1 to 6 carbon atoms) beside the carbon atom of a carbonyl group; or are bonded together to form a divalent hydrocarbon group, $R^{16}$-$R^{18}$, preferably having 1 to 18 carbon atoms, more preferably having 2 to 6 carbon atoms. $R^{17}$ and $R^{19}$ are each independently a monovalent hydrocarbon group preferably having 1 to 18 carbon atoms, more preferably having 1 to 6 carbon atoms, or an acyl group having 1 to 18 carbon atoms (more preferably having 1 to 6 carbon atoms) beside the carbon atom of a carbonyl group; or are bonded together to form a divalent hydrocarbon group, $R^{17}$-$R^{19}$, preferably having 1 to 18 carbon atoms, more preferably having 2 to 6 carbon atoms. Examples of the monovalent hydrocarbon group, the acyl group and the divalent hydrocarbon group include examples of the monovalent hydrocarbon group, the acyl group and the divalent hydrocarbon group of $R^1$, $R^2$, $R^3$ and $R^4$ in General Formula (1).

The hydroxy group of $Y^1$ is expressed by —OH. The hydroxy group may be protected by an acetyl group, a tetrahydropyranyloxy group, a tosyl group, a silyl group described later, or the like.

The acyl group of $Y^1$ is expressed by —$COR^{20}$. In this formula, $R^{20}$ is a monovalent hydrocarbon group preferably having 1 to 18 carbon atoms, more preferably having 1 to 6 carbon atoms. Examples of the monovalent hydrocarbon group include examples of the monovalent hydrocarbon group of $R^1$, $R^2$, $R^3$ and $R^4$ in General Formula (1).

The acyloxy group of $Y^1$ is expressed by —$OCOR^{21}$. In this formula, $R^{21}$ is a monovalent hydrocarbon group preferably having 1 to 18 carbon atoms, more preferably having 1 to 6 carbon atoms. Examples of the monovalent hydrocarbon group include examples of the monovalent hydrocarbon group of $R^1$, $R^2$, $R^3$ and $R^4$ in General Formula (1).

The alkoxy group of $Y^1$ is expressed by —O—$R^{22}$. In this formula, $R^{22}$ is a monovalent hydrocarbon group preferably having 1 to 18 carbon atoms, more preferably having 1 to 6 carbon atoms. Examples of the monovalent hydrocarbon group include examples of the monovalent hydrocarbon group of $R^1$, $R^2$, $R^3$ and $R^4$ in General Formula (1).

The alkoxyalkoxy group of $Y^1$ is expressed by —O—$Z^5$—O—$R^{23}$. In this formula, $R^{23}$ is a monovalent hydrocarbon group preferably having 1 to 18 carbon atoms, more preferably having 1 to 6 carbon atoms. Examples of the monovalent hydrocarbon group include examples of the monovalent hydrocarbon group of $R^1$, $R^2$, $R^3$ and $R^4$ in General Formula (1). $Z^5$ is a divalent hydrocarbon group preferably having 1 to 18 carbon atoms, more preferably having 1 to 6 carbon atoms. Examples of the divalent hydrocarbon group include a methylene group and examples of the divalent hydrocarbon group of $R^1$, $R^2$, $R^3$ and $R^4$ in General Formula (1).

The carboxyl group of $Y^1$ is expressed by —COOH. The carboxyl group may be protected by a tert-butyl group or the like.

The amino group of $Y^1$ is expressed by —$NH_2$.

The monosubstituted amino group of $Y^1$ having a monovalent hydrocarbon group having 1 to 18 carbon atoms is expressed by —$NHR^{24}$. In this formula, $R^{24}$ is a monovalent hydrocarbon group preferably having 1 to 18 carbon atoms, more preferably having 1 to 6 carbon atoms. Examples of the monovalent hydrocarbon group include examples of the monovalent hydrocarbon group of $R^1$, $R^2$, $R^3$ and $R^4$ in General Formula (1).

The disubstituted amino group of $Y^1$ having two monovalent hydrocarbon groups each having 1 to 18 carbon atoms is expressed by —$NR^{25}R^{26}$. In this formula, $R^{25}$ and $R^{26}$ are each independently a monovalent hydrocarbon group having 1 to 18 carbon atoms, more preferably having 1 to 6 carbon atoms; or are bonded together to form a divalent hydrocarbon group, $R^{25}$-$R^{26}$, preferably having 2 to 18 carbon atoms, more preferably having 2 to 6 carbon atoms. Examples of the monovalent hydrocarbon group and the divalent hydrocarbon group include examples of the monovalent hydrocarbon group and the divalent hydrocarbon group of $R^1$, $R^2$, $R^3$ and $R^4$ in General Formula (1).

The acylamino group of $Y^1$ is expressed by —NHC=O ($R^{27}$). In this formula, $R^{27}$ is a monovalent hydrocarbon group preferably having 1 to 18 carbon atoms, more preferably having 1 to 6 carbon atoms. Examples of the monovalent hydrocarbon group include examples of the monovalent hydrocarbon group of $R^1$, $R^2$, $R^3$ and $R^4$ in General Formula (1).

The silyl group of $Y^1$ is expressed by —Si($R^{28}$)($R^{29}$) ($R^{30}$). In this formula, $R^{28}$ is a hydrogen atom or a monovalent hydrocarbon group preferably having 1 to 18 carbon atoms, more preferably having 1 to 6 carbon atoms; and $R^{29}$ and $R^{30}$ are each independently a monovalent hydrocarbon group preferably having 1 to 18 carbon atoms, more preferably having 1 to 6 carbon atoms, or are bonded together to form a divalent hydrocarbon group, $R^{29}$-$R^{30}$, preferably having 1 to 18 atoms, more preferably having 1 to 6 carbon atoms. Examples of the monovalent hydrocarbon group and the divalent hydrocarbon group include examples of the monovalent hydrocarbon group and the divalent hydrocarbon group of $R^1$, $R^2$, $R^3$ and $R^4$ in General Formula (1). Examples of the silyl group include trialkylsilyl groups and monoalkyldiarylsilyl groups.

The alkoxycarbonyloxy group of $Y^1$ is expressed by —$OCOOR^{31}$. In this formula, $R^{31}$ is a monovalent hydrocarbon group preferably having 1 to 18 carbon atoms, more preferably having 1 to 6 carbon atoms. Examples of the monovalent hydrocarbon group include examples of the monovalent hydrocarbon group of $R^1$, $R^2$, $R^3$ and $R^4$ in General Formula (1).

In General Formula (1), a, b, c, d, e and f are each an integer of 0 to 8, preferably an integer of 0 to 6; and g is an integer of 1 to 8, preferably an integer of 1 to 3. However, not all of a, c, d, and f are 0. In other words, a=c=d=f=0 is excluded.

Examples of the halide compound General Formula (1) having a carbon-carbon unsaturated bond include a monoene halide compound (for example, a=1, b=c=d=e=f=0, and g=1), a skipped diene halide compound (for example, a=b=d=1, c=e=f=0, and g=1), a monoyne halide compound (for example, c=1, a=b=d=e=f=0, and, g=1), a skipped diyne halide compound (for example, c=e=f=1, a=b=d=0, and g=1), a conjugated diyne halide compound (for example, c=2, a=b=d=e=f=0, and g=1), and the other halide compound having an ene-yne structure. In the following examples, unsaturated halide compounds each having the total number of double (C=C) and triple (C≡C) bonds of 1 or 2 in the skeleton thereof are exemplified, but the other unsaturated compounds each having the total number of double and triple bonds of three or more can undergo the present reaction.

Examples of the monoene halide compound include a 6-halo-1,1-dialkoxy-2-hexene such as (2Z)-6-chloro-1,1-diethoxy-2-hexene; a 1-halo-3-nonene such as (3Z)-1-chloro-3-nonene; a 1-halo-4-decene such as (4Z)-1-bromo-4-decene; and an 8-halo-2,6-dimethyl-2-octene such as 8-chloro-2,6-dimethyl-2-octene.

Examples of the skipped diene halide compound include a 1-halo-3,6-nonadiene such as (3Z,6Z)-1-chloro-3,6-nonadiene.

Examples of the monoyne halide compound include a 6-halo-1,1-dialkoxy-2-hexyne such as 6-chloro-1,1-diethoxy-2-hexyne; a 8-halo-1,1-dialkoxy-2-octyne such as 8-chloro-1,1-diethoxy-2-octyne; a 7-halo-1,1-dialkoxy-2-heptyne such as 7-chloro-1,1-diethoxy-2-heptyne; a 9-halo-1,1-dialkoxy-2-nonyne such as 9-chloro-1,1-diethoxy-2-nonyne; a 14-halo-1,1-dialkoxy-7-tetradecyne such as 14-chloro-1,1-diethoxy-7-tetradecyne; a 1-halo-7-hexadecyne such as 1-chloro-7-hexadecyne; a 1-halo-7-octyne such as 1-chloro-7-octyne; a 1-halo-10-alkyl-7-tetradecyne such as 1-chloro-10-methyl-7-tetradecyne; a 2-halo-6-undecyne such as 2-chloro-6-undecyne; a 1-trialkylsilyl-8-halo-1-octyne such as 1-trimethyl silyl-8-chloro-1-octyne; and a 1-hydroxy-10-halo-3-decyne such as 1-hydroxy-10-chloro-3-decyne.

Examples of the skipped diyne halide compound include a 1-halo-7,10-tridecadiyne such as 1-chloro-7,10-tridecadiyne.

Examples of the conjugated diyne halide compound include a 12-halo-1-(alkoxyalkoxy)-3,5-dodecadiyne such as 12-chloro-1-(methoxymethoxy)-3,5-dodecadiyne.

Of these examples, from the viewpoint of sufficient suppression of dehalogenation and production of a halide compound at a satisfactory yield, a 6-halo-1,1-dialkoxy-2-hexyne, an 8-halo-1,1-dialkoxy-2-octyne, a 7-halo-1,1-dialkoxy-2-heptyne, a 9-halo-1,1-dialkoxy-2-nonyne, a 1-hydroxy-10-halo-3-decyne, and an 8-halo-2,6-dimethyl-2-octenes are preferred, and a 6-halo-1,1-dialkoxy-2-hexyne, a 9-halo-1,1-dialkoxy-2-nonyne, a 1-hydroxy-10-halo-3-decyne, and an 8-halo-2,6-dimethyl-2-octene are more preferred.

The catalytic reduction may be carried out by a known method, for example, in a hydrogen gas atmosphere.

The reaction temperature of the catalytic reduction is preferably 10 to 180° C. and more preferably 20 to 80° C. from the viewpoint of reaction efficiency.

The reaction time of the catalytic reduction varies depending on reaction scales, stirring rates, or feed amounts of hydrogen. The reaction time is preferably 1 to 120 hours from the viewpoint of productivity.

In General Formula (2), X is a halogen atom and examples thereof include those of X in General Formula (1).

In General Formula (2), $R^5$, $R^6$, $R^7$ and $R^8$ are each independently a hydrogen atom, a halogen atom, a monovalent hydrocarbon group having 1 to 18 carbon atoms, preferably having 1 to 6 carbon atoms, or an acyl group having 1 to 18 carbon atoms (preferably having 1 to 6 carbon atoms) beside the carbon atom of a carbonyl group; or are bonded together to form a divalent hydrocarbon group, $R^5$-$R^6$, $R^5$-$R^7$, $R^5$-$R^8$, $R^6$-$R^7$, $R^6$-$R^8$, or $R^7$-$R^8$, having 1 to 18 carbon atoms, preferably having 1 to 6 carbon atoms.

Examples of the monovalent hydrocarbon group, the acyl group and the divalent hydrocarbon group include examples of the monovalent hydrocarbon group, the acyl group and the divalent hydrocarbon group of $R^1$, $R^2$, $R^3$ and $R^4$ in General Formula (1).

In General Formula (2), $Z^3$ and $Z^4$ are each independently a divalent hydrocarbon group having 1 to 18 carbon atoms, or a single bond, and examples of the divalent hydrocarbon include a methylene group and examples of the divalent hydrocarbon of $R^1$, $R^2$, $R^3$ and $R^4$ in General Formula (1).

In General Formula (2), $Y^2$ is a hydrogen atom, a halogen atom, a protected formyl group, a hydroxy group, an acyl group, an acyloxy group, an alkoxy group, an alkoxyalkoxy group, a carboxyl group, an amino group, an amino group monosubstituted with a monovalent hydrocarbon group having 1 to 18 carbon atoms, an amino group disubstituted with two monovalent hydrocarbon groups each having 1 to 18 carbon atoms, an acylamino group, a silyl group, and an alkoxycarbonyloxy group. Examples of $Y^2$ in General Formula (2) include examples of $Y^2$ in General Formula (1).

In General Formula (2), a, b, c, d, e and f are each an integer of 0 to 8; and g is an integer of 1 to 3, preferably an integer of 1 to 3; but not all of a, c, d and f are 0. In other words, a=c=d=f=0 is excluded.

X, $R^1$, $R^2$, $R^3$, $R^4$, $R^1$-$R^2$, $R^1$-$R^3$, $R^1$-$R^4$, $R^2$-$R^3$, $R^2$-$R^4$, $R^3$-$R^4$, $Z^1$, $Z^2$, $Y^1$, a, b, c, d, e, f and g in General Formula (1) basically correspond to X, $R^5$, $R^6$, $R^7$, $R^8$, $R^5$-$R^6$, $R^5$-$R^7$, $R^5$-$R^8$, $R^6$-$R^7$, $R^6$-$R^8$, $R^7$-$R^8$, $Z^3$, $Z^4$, $Y^2$, a, b, c, d, e, f and g in General Formula (2), before and after catalytic reduction. However, when $R^1$, $R^2$, $R^3$, $R^4$, $R^1$-$R^2$, $R^1$-$R^3$, $R^1$-$R^4$, $R^2$-$R^3$, $R^2$-$R^4$, $R^3$-$R^4$, $Z^1$, $Z^2$ or $Y^1$ has one or more carbon-carbon unsaturated bonds in General Formula (1), at least one of the one or more carbon-carbon unsaturated bonds may undergo catalytic reduction into a carbon-carbon saturated bond.

Examples of the halide compound (2) in which at least one of carbon-carbon unsaturated bonds is reduced include a 6-halo-1,1-dialkoxyhexane such as 6-chloro-1,1-diethoxyhexane; an 8-halo-1,1-dialkoxyoctane such as 8-chloro-1,1-diethoxyoctane; a 7-halo-1,1-dialkoxyheptane such as 7-chloro-1,1-diethoxyheptane; a 9-halo-1,1-dialkoxynonane such as 9-chloro-1,1-diethoxynonane; a 14-halo-1,1-dialkoxytetradecane such as 14-chloro-1,1-diethoxytetradecane; a 1-halotridecane such as 1-chlorotridecane; a 12-halo-1-(alkoxyalkoxy)dodecane such as 12-chloro-1-(methoxymethoxy)dodecane; a 1-halononane such as 1-chlorononane; a 1-halohexadecane such as 1-chlorohexadecane; a 1-halooctane such as 1-chlorooctane; a 1-halo-10-alkyltetradecane such as 1-chloro-10-methyltetradecane; a 2-haloundecane such as 2-chloroundecane; a 1-halodecane such as 1-bromodecane; a 1-trialkylsilyl-8-halooctane such as 1-trimethylsilyl-8-chlorooctane; a 1-hydroxy-10-halodecane such as 1-hydroxy-10-chlorodecane; and a 1-halo-3,7-dimethyloctane such as 1-chloro-3,7-dimethyloctane.

As described above, the method for producing a reduced halide compound having undergone reduction of at least one carbon-carbon unsaturated bond by catalytic reduction in the presence of the NiZn catalyst is provided.

EXAMPLES

The invention will next be specifically described with reference to Examples. It should not be construed that the invention is limited to or by them.

Example 1 <Production of Cl(CH$_2$)$_5$CH(OCH$_2$CH$_3$)$_2$>

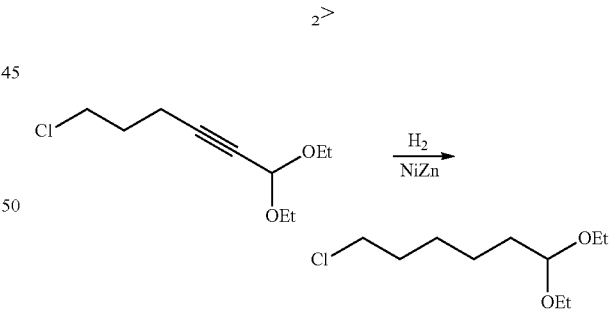

Nickel(II) acetate (12.0 g, 0.048 mol), zinc(II) oxide (3.91 g, 0.048 mol), and ethanol (341.1 g, 7.40 mol) were placed in a reactor, heated at 50 to 55° C., and stirred for 1 hour. Next, the mixture was cooled to 40° C., subjected to addition of sodium borohydride (2.33 g, 0.061 mol), and stirred at 35 to 45° C. for 2 hours. Subsequently, 6-chloro-1,1-diethoxy-2-hexyne (comp. of Formula 1) (806.5 g, 3.94 mol) was added into the reactor in which the NiZn catalyst had been prepared, then the mixture was warmed to 40 to 50° C., and hydrogen gas was fed thereto for 9 hours while the progress of the reaction was observed. The resulting mixture was cooled to 40° C. or less, and the NiZn catalyst was filtered off, then water (128.6 g) was added to the filtrate for liquid separation. The organic phase was concentrated under reduced pressure, and then the residue was subjected to vacuum distillation to obtain 6-chloro-1,1-diethoxyhexane (comp. of Formula 2) (783.4 g, 3.75 mol) at a yield of 95.3%.

The yield of 1,1-diethoxyhexane, which was a dehalogenation product, was 0.21%, so that almost no by-product was yielded.

6-chloro-1,1-diethoxyhexane (comp. of Formula 2)

[Nuclear magnetic resonance spectrum] $^1$H-NMR (500 MHz, CDCl$_3$): δ=1.18 (6H, t, J=7.1 Hz), 1.29-1.42 (2H, m), 1.42-1.48 (2H, m), 1.60 (2H, dt, J=5.7 Hz, 7.8 Hz), 1.76 (2H, quint-like, J=7.1 Hz), 3.47 (2H, dq, J=7.2 Hz, 7.9 Hz), 3.51 (2H, t, J=6.7 Hz), 3.62 (2H, dq, J=7.1 Hz, 7.8 Hz), 4.46 (1H, t, J=5.8 Hz); $^{13}$C-NMR (125 MHz, CDCl$_3$): δ=15.29, 23.97, 26.66, 32.48, 33.38, 44.94, 60.91, 102.70

[Mass spectrum] EI-mass spectrum (70 eV): m/z 207 (M$^+$-1), 163, 117, 103, 75, 59, 29

[Infrared absorption spectrum] (NaCl): ν=2975, 2933, 2870, 1445, 1128, 1061, 1000, 731, 652

Example 2 <Production of Cl(CH$_2$)$_7$CH(OCH$_2$CH$_3$)$_2$>

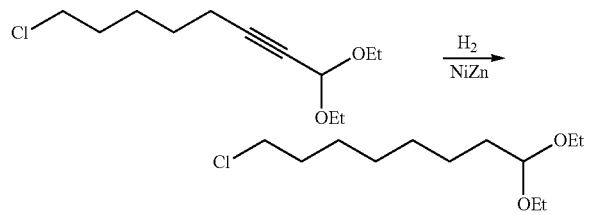

Nickel(II) acetate (4.64 g, 0.019 mol), zinc(II) oxide (1.52 g, 0.019 mol), and ethanol (132.3 g, 2.87 mol) were placed in a reactor, heated at 50 to 55° C., and stirred for 1 hour. Next, the mixture was cooled to 40° C., subjected to addition of sodium borohydride (0.90 g, 0.024 mol), and stirred at 35 to 45° C. for 2 hours. Subsequently, 8-chloro-1,1-diethoxy-2-octyne (comp. of Formula 1) (354.9 g, 1.53 mol) was added into the reactor in which the NiZn catalyst had been prepared, then the mixture was warmed to 40 to 50° C., and hydrogen gas was fed thereto for 27 hours while the progress of the reaction was observed. The resulting mixture was cooled to 40° C. or less, and the NiZn catalyst was filtered off, then water (50.7 g) was added to the filtrate for liquid separation. The organic phase was concentrated under reduced pressure, and then the residue was subjected to vacuum distillation to obtain 8-chloro-1,1-diethoxyoctane (comp. of Formula 2) (345.5 g, 1.46 mol) at a yield of 95.6%.

The yield of 1,1-diethoxyoctane, which was a dehalogenation product, was 0.83%, so that almost no by-product was yielded.

8-chloro-1,1-diethoxyoctane (comp. of Formula 2)

[Nuclear magnetic resonance spectrum] $^1$H-NMR (500 MHz, CDCl$_3$): δ=1.19 (6H, t, J=7.1 Hz), 1.27-1.37 (6H, m), 1.37-1.45 (2H, m), 1.56-1.62 (2H, m), 1.75 (2H, quint-like, J=7.2 Hz), 3.47 (2H, dq, J=6.9 Hz, 7.9 Hz), 3.51 (2H, t, J=6.9 Hz), 3.62 (2H, dq, J=7.1 Hz, 7.8 Hz), 4.46 (1H, t-like, J=5.7 Hz); $^{13}$C-NMR (125 MHz, CDCl$_3$): δ=15.31, 24.58, 26.73, 28.75, 29.24, 32.54, 33.50, 45.08, 60.79, 102.84

[Mass spectrum] EI-mass spectrum (70 eV): m/z 235 (M$^+$-1), 191, 145, 103, 91, 75, 59

[Infrared absorption spectrum] (NaCl): ν=2975, 2932, 2859, 1445, 1128, 1062, 1004, 726, 653

Example 3 <Production of Cl(CH$_2$)$_6$CH(OCH$_2$CH$_3$)$_2$>

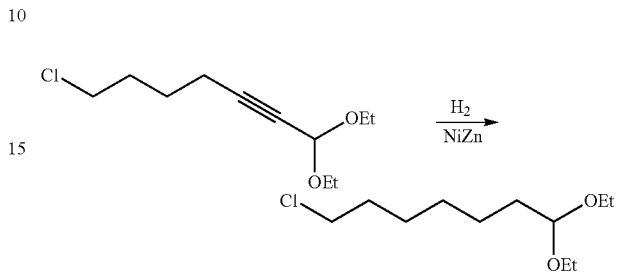

Nickel(II) acetate (5.42 g, 0.022 mol), zinc(II) oxide (1.77 g, 0.022 mol), and ethanol (154.7 g, 3.35 mol) were placed in a reactor, heated at 50 to 55° C., and stirred for 1 hour. Next, the mixture was cooled to 40° C., subjected to addition of sodium borohydride (1.1 g, 0.028 mol), and stirred at 35 to 45° C. for 2 hours. Subsequently, 7-chloro-1,1-diethoxy-2-heptyne (comp. of Formula 1) (390.2 g, 1.78 mol) was added into the reactor in which the NiZn catalyst had been prepared, then the mixture was warmed to 40 to 50° C., and hydrogen gas was fed thereto for 25.5 hours while the progress of the reaction was observed. The resulting mixture was cooled to 40° C. or less, and the NiZn catalyst was filtered off, then water (59.3 g) was added to the filtrate for liquid separation. The organic phase was concentrated under reduced pressure, and then the residue was subjected to vacuum distillation to obtain 7-chloro-1,1-diethoxyheptane (comp. of Formula 2) (383.6 g, 1.72 mol) at a yield of 96.6%.

The yield of 1,1-diethoxyheptane, which was a dehalogenation product, was 0.61%, so that almost no by-product was yielded.

7-chloro-1,1-diethoxyheptane (comp. of Formula 2)

[Nuclear magnetic resonance spectrum] $^1$H-NMR (500 MHz, CDCl$_3$): δ=1.19 (6H, t, J=7.1 Hz), 1.28-1.38 (4H, m), 1.38-1.46 (2H, m), 1.59 (2H, dt, J=9.0 Hz, 6.0 Hz), 1.75 (2H, quint-like, J=7.2 Hz), 3.47 (2H, dq, J=7.1 Hz, 7.8 Hz), 3.51 (2H, t, J=6.7 Hz), 3.62 (2H, dq, J=7.1 Hz, 7.8 Hz), 4.46 (1H, t-like, J=5.7 Hz); $^{13}$C-NMR (125 MHz, CDCl$_3$): δ=15.31, 24.52, 26.75, 28.68, 32.48, 33.44, 45.04, 60.84, 102.80

[Mass spectrum] EI-mass spectrum (70 eV): m/z 221 (M$^+$-1), 177, 131, 119, 103, 75, 59

[Infrared absorption spectrum] (NaCl): ν=2975, 2934, 2863, 1445, 1128, 1062, 1005, 728, 652

Example 4 <Production of Cl(CH$_2$)$_8$CH(OCH$_2$CH$_3$)$_2$>

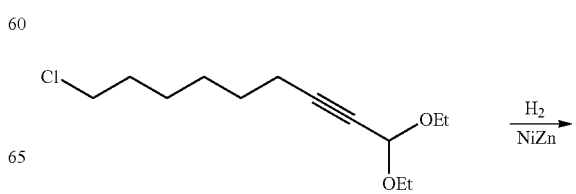

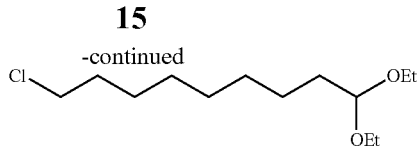

Nickel(II) acetate (84.6 g, 0.34 mol), zinc(II) oxide (27.7 g, 0.34 mol), and ethanol (2,414.6 g, 52.41 mol) were placed in a reactor, heated at 50 to 55° C., and stirred for 1 hour. Next, the mixture was cooled to 40° C., subjected to addition of sodium borohydride (16.5 g, 0.44 mol), and stirred at 35 to 45° C. for 2 hours to obtain a NiZn catalyst. The mixture was cooled to 30° C. or less, and the thus-obtained NiZn catalyst (495.9 g) and 9-chloro-1,1-diethoxy-2-nonyne (comp. of Formula 1) (892.8 g, 3.62 mol) were placed in another reactor. The mixture was warmed to 40 to 50° C., and hydrogen gas was fed thereto for 29 hours while the progress of the reaction was observed. The resulting mixture was cooled to 40° C. or less, and the NiZn catalyst was filtered off, then water (120.2 g) was added to the filtrate for liquid separation. The organic phase was concentrated under reduced pressure, and then the residue was subjected to vacuum distillation to obtain 9-chloro-1,1-diethoxynonane (comp. of Formula 2) (864.8 g, 3.45 mol) at a yield of 95.3%.

The yield of 1,1-diethoxynonane, which was a dehalogenation product, was 0.18%, so that almost no by-product was yielded.

9-chloro-1,1-diethoxynonane (comp. of Formula 2)

[Nuclear magnetic resonance spectrum] $^1$H-NMR (500 MHz, CDCl$_3$): δ=1.19 (6H, t, J=7.1 Hz), 1.25-1.36 (8H, m), 1.36-1.44 (2H, m), 1.55-1.62 (2H, m), 1.75 (2H, quint-like, J=7.1 Hz), 3.47 (2H, dq, J=7.1 Hz, 7.8 Hz), 3.51 (2H, t, J=6.7 Hz), 3.62 (2H, dq, J=7.1 Hz, 7.8 Hz), 4.46 (1H, t, J=5.8 Hz); $^{13}$C-NMR (125 MHz, CDCl$_3$): δ=15.32, 24.64, 26.79, 28.74, 29.32, 32.57, 33.52, 45.10, 60.78, 102.87

[Mass spectrum] EI-mass spectrum (70 eV): m/z 249 (M$^+$−1), 205, 161, 123, 103, 75, 59

[Infrared absorption spectrum] (NaCl): ν=2975, 2930, 2857, 1445, 1128, 1061, 725, 653

Example 5 <Production of Cl(CH$_2$)$_5$CH(OCH$_2$CH$_3$)$_2$>

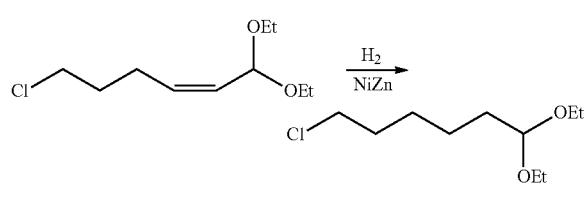

Nickel(II) acetate (6.36 g, 0.026 mol), zinc(II) oxide (2.08 g, 0.026 mol), and ethanol (181.5 g, 3.94 mol) were placed in a reactor, heated at 50 to 55° C., and stirred for 1 hour. Next, the mixture was cooled to 40° C., subjected to addition of sodium borohydride (1.24 g, 0.033 mol), and stirred at 35 to 45° C. for 2 hours. Subsequently, (2Z)-6-chloro-1,1-diethoxy-2-hexene (comp. of Formula 1) (630.5 g, 3.05 mol) was added into the reactor in which the NiZn catalyst had been prepared, then the mixture was warmed to 40 to 50° C., and hydrogen gas was fed thereto for 3 hours while the progress of the reaction was observed. The resulting mixture was cooled to 40° C. or less, and the NiZn catalyst was filtered off, then water (110.0 g) was added to the filtrate for liquid separation. The organic phase was concentrated under reduced pressure, and then the residue was subjected to vacuum distillation to obtain 6-chloro-1,1-diethoxyhexane (comp. of Formula 2) (561.5 g, 2.69 mol) at a yield of 88.2%.

The yield of 1,1-diethoxyhexane, which was a dehalogenation product, was 2.97%, so that the by-product was only slightly yielded.

6-chloro-1,1-diethoxyhexane (comp. of Formula 2)

[Nuclear magnetic resonance spectrum] $^1$H-NMR (500 MHz, CDCl$_3$): δ=1.18 (6H, t, J=7.1 Hz), 1.29-1.42 (2H, m), 1.42-1.48 (2H, m), 1.60 (2H, dt, J=5.7 Hz, 7.8 Hz), 1.76 (2H, quint-like, J=7.1 Hz), 3.47 (2H, dq, J=7.2 Hz, 7.9 Hz), 3.51 (2H, t, J=6.7 Hz), 3.62 (2H, dq, J=7.1 Hz, 7.8 Hz), 4.46 (1H, t, J=5.8 Hz); $^{13}$C-NMR (125 MHz, CDCl$_3$): δ=15.29, 23.97, 26.66, 32.48, 33.38, 44.94, 60.91, 102.70

[Mass spectrum] EI-mass spectrum (70 eV): m/z 207 (M$^+$−1), 163, 117, 103, 75, 59, 29

[Infrared absorption spectrum] (NaCl): ν=2975, 2933, 2870, 1445, 1128, 1061, 1000, 731, 652

Example 6 <Production of Cl(CH$_2$)$_5$CH(OCH$_2$CH$_3$)$_2$>

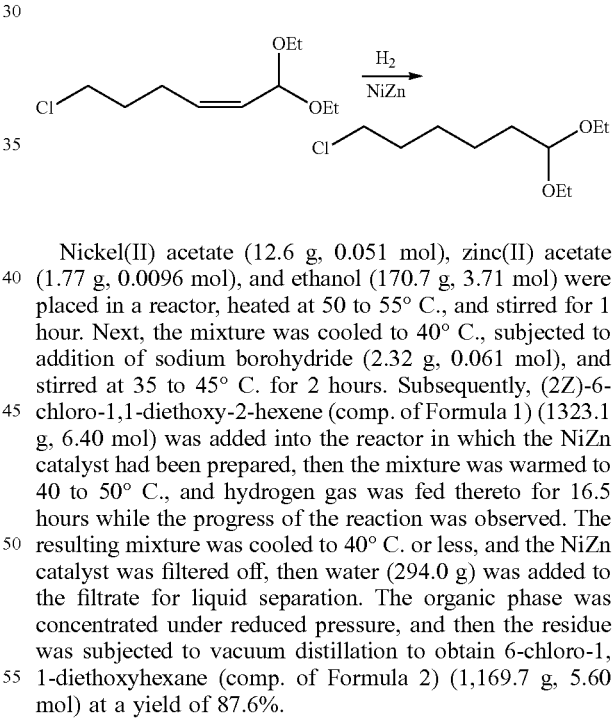

Nickel(II) acetate (12.6 g, 0.051 mol), zinc(II) acetate (1.77 g, 0.0096 mol), and ethanol (170.7 g, 3.71 mol) were placed in a reactor, heated at 50 to 55° C., and stirred for 1 hour. Next, the mixture was cooled to 40° C., subjected to addition of sodium borohydride (2.32 g, 0.061 mol), and stirred at 35 to 45° C. for 2 hours. Subsequently, (2Z)-6-chloro-1,1-diethoxy-2-hexene (comp. of Formula 1) (1323.1 g, 6.40 mol) was added into the reactor in which the NiZn catalyst had been prepared, then the mixture was warmed to 40 to 50° C., and hydrogen gas was fed thereto for 16.5 hours while the progress of the reaction was observed. The resulting mixture was cooled to 40° C. or less, and the NiZn catalyst was filtered off, then water (294.0 g) was added to the filtrate for liquid separation. The organic phase was concentrated under reduced pressure, and then the residue was subjected to vacuum distillation to obtain 6-chloro-1,1-diethoxyhexane (comp. of Formula 2) (1,169.7 g, 5.60 mol) at a yield of 87.6%.

The yield of 1,1-diethoxyhexane, which was a dehalogenation product, was 3.05%, so that the by-product was only slightly yielded.

6-chloro-1,1-diethoxyhexane (comp. of Formula 2)

[Nuclear magnetic resonance spectrum] $^1$H-NMR (500 MHz, CDCl$_3$): δ=1.18 (6H, t, J=7.1 Hz), 1.29-1.42 (2H, m), 1.42-1.48 (2H, m), 1.60 (2H, dt, J=5.7 Hz, 7.8 Hz), 1.76 (2H, quint-like, J=7.1 Hz), 3.47 (2H, dq, J=7.2 Hz, 7.9 Hz), 3.51 (2H, t, J=6.7 Hz), 3.62 (2H, dq, J=7.1 Hz, 7.8 Hz), 4.46 (1H, t, J=5.8 Hz); $^{13}$C-NMR (125 MHz, CDCl$_3$): δ=15.29, 23.97, 26.66, 32.48, 33.38, 44.94, 60.91, 102.70

[Mass spectrum] EI-mass spectrum (70 eV): m/z 207 (M$^+$−1), 163, 117, 103, 75, 59, 29

[Infrared absorption spectrum] (NaCl): ν=2975, 2933, 2870, 1445, 1128, 1061, 1000, 731, 652

Example 7 <Production of Cl(CH$_2$)$_{13}$CH(OCH$_2$CH$_3$)$_2$>

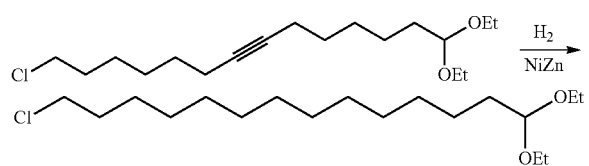

Nickel(II) acetate (0.90 g, 0.0036 mol), zinc(II) oxide (0.29 g, 0.0036 mol), and ethanol (25.6 g, 0.56 mol) were placed in a reactor, heated at 50 to 55° C., and stirred for 1 hour. Next, the mixture was cooled to 40° C., subjected to addition of sodium borohydride (0.17 g, 0.0045 mol), and stirred at 35 to 45° C. for 2 hours. Subsequently, 14-chloro-1,1-diethoxy-7-tetradecyne (comp. of Formula 1) (93.4 g, 0.29 mol) was added into the reactor in which the NiZn catalyst had been prepared, then the mixture was warmed to 40 to 50° C., and hydrogen gas was fed thereto for 18.5 hours while the progress of the reaction was observed. The resulting mixture was cooled to 40° C. or less, and the NiZn catalyst was filtered off, then water (9.8 g) was added to the filtrate for liquid separation. The organic phase was concentrated under reduced pressure, and then the residue was subjected to vacuum distillation to obtain 14-chloro-1,1-diethoxytetradecane (comp. of Formula 2) (84.5 g, 0.26 mol) at a yield of 89.4%.

The yield of 1,1-diethoxytetradecane, which was a dehalogenation product, was 0.45%, so that almost no by-product was yielded.

14-chloro-1,1-diethoxytetradecane (comp. of Formula 2)

[Nuclear magnetic resonance spectrum] $^1$H-NMR (500 MHz, CDCl$_3$): δ=1.19 (6H, t, J=7.1 Hz), 1.22-1.36 (18H, m), 1.36-1.44 (2H, m), 1.56-1.62 (2H, m), 1.75 (2H, quint-like, J=7.2 Hz), 3.47 (2H, dq, J=7.1 Hz, 7.8 Hz), 3.51 (2H, t, J=6.9 Hz), 3.62 (2H, dq, J=7.1 Hz, 7.9 Hz), 4.46 (1H, t, J=5.7 Hz); $^{13}$C-NMR (125 MHz, CDCl$_3$): δ=15.32, 24.72, 26.85, 28.85, 29.42, 29.45, 29.50, 29.52, 29.57, 32.61, 33.54, 45.14, 60.74, 102.91

[Mass spectrum] EI-mass spectrum (70 eV): m/z 319 (M$^+$−1), 275, 111, 103, 97, 75,

[Infrared absorption spectrum] (NaCl): ν=2975, 2926, 2854, 1466, 1127, 1062, 723, 654

Example 8 <Production of Cl(CH$_2$)$_{12}$CH$_3$>

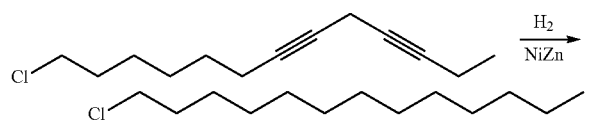

Nickel(II) acetate (1.70 g, 0.0068 mol), zinc(II) oxide (0.55 g, 0.0068 mol), and methanol (48.4 g, 1.51 mol) were placed in a reactor, heated at 50 to 55° C., and stirred for 1 hour. Next, the mixture was cooled to 40° C., subjected to addition of sodium borohydride (0.33 g, 0.0087 mol), and stirred at 35 to 45° C. for 2 hours. Subsequently, 1-chloro-7,10-tridecadiyne (comp. of Formula 1) (117.6 g, 0.56 mol) was added into the reactor in which the NiZn catalyst had been prepared, then the mixture was warmed to 40 to 50° C., and hydrogen gas was fed thereto for 22 hours while the progress of the reaction was observed. The resulting mixture was cooled to 40° C. or less, and the NiZn catalyst was filtered off, then water (20.0 g) was added to the filtrate for liquid separation. The organic phase was concentrated under reduced pressure, and then the residue was subjected to vacuum distillation to obtain 1-chlorotridecane (comp. of Formula 2) (113.7 g, 0.52 mol) at a yield of 93.1%.

The yield of tridecane, which was a dehalogenation product, was 0.28%, so that almost no by-product was yielded.

1-chlorotridecane (comp. of Formula 2)

[Nuclear magnetic resonance spectrum] $^1$H-NMR (500 MHz, CDCl$_3$): δ=0.88 (3H, t, J=7.1 Hz), 1.22-1.34 (18H, m), 1.38-1.46 (2H, m), 1.77 (2H, quint-like, J=7.2 Hz), 3.53 (2H, t, J=6.9 Hz); $^{13}$C-NMR (125 MHz, CDCl$_3$): δ=14.11, 22.69, 26.90, 28.90, 29.34, 29.47, 29.56, 29.64, 29.66, 31.92, 32.66, 45.17

[Mass spectrum] EI-mass spectrum (70 eV): m/z 218 (M+), 203, 189, 175, 161, 147, 133, 119, 105, 91, 85, 71, 57, 43, 29

[Infrared absorption spectrum] (NaCl): ν=2955, 2924, 2854, 1466, 723, 655

Example 9 <Production of Cl(CH$_2$)$_{12}$OCH$_2$OCH$_3$>

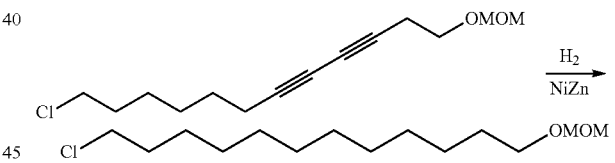

Nickel(II) acetate (1.06 g, 0.0043 mol), zinc(II) oxide (0.35 g, 0.0043 mol), and methanol (30.2 g, 0.94 mol) were placed in a reactor, heated at 50 to 55° C. and stirred for 1 hour. Next, the mixture was cooled to 40° C., subjected to addition of sodium borohydride (0.21 g, 0.0056 mol), and stirred at 35 to 45° C. for 2 hours. Subsequently, 12-chloro-1-(methoxymethoxy)-3,5-dodecadiyne (comp. of Formula 1) (89.3 g, 0.35 mol) was added into the reactor in which the NiZn catalyst had been prepared, then the mixture was warmed to 40 to 50° C., and hydrogen gas was fed thereto for 16.5 hours while the progress of the reaction was observed. The resulting mixture was cooled to 40° C. or less, and the NiZn catalyst was filtered off, then water (11.5 g) was added to the filtrate for liquid separation. The organic phase was concentrated under reduced pressure, and then the residue was subjected to vacuum distillation to obtain 12-chloro-1-(methoxymethoxy)dodecane (comp. of Formula 2) (81.3 g, 0.31 mol) at a yield of 88.3%.

The 1-(methoxymethoxy)dodecane, which was a dehalogenation product, was not yielded as a by-product.

12-chloro-1-(methoxymethoxy)dodecane (comp. of Formula 2)

[Nuclear magnetic resonance spectrum] $^1$H-NMR (500 MHz, CDCl$_3$): δ=1.23-1.37 (14H, m), 1.37-1.44 (2H, m), 1.58 (2H, quint-like, J=7.1 Hz), 1.75 (2H, quint-like, J=7.2 Hz), 3.35 (3H, s), 3.50 (2H, t, J=6.9 Hz), 3.52 (2H, t, J=6.9 Hz), 4.61 (2H, s); $^{13}$C-NMR (125 MHz, CDCl$_3$): δ=26.17, 26.84, 28.85, 29.39, 29.41, 29.47, 29.50, 29.53, 29.70, 32.61, 45.14, 55.03, 67.81, 96.33

[Mass spectrum] EI-mass spectrum (70 eV): m/z 263 (M$^+$-1), 214, 200, 186, 172, 97, 83, 69, 45, 29

[Infrared absorption spectrum] (NaCl): ν=2927, 2854, 1466, 1150, 1112, 1046, 920, 724, 653

Production of Example 10 <Cl(CH$_2$)$_8$CH$_3$>

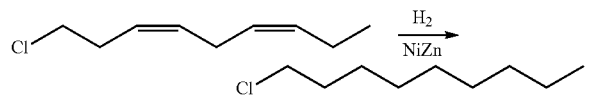

Nickel(II) acetate (3.66 g, 0.015 mol), zinc(II) oxide (1.20 g, 0.015 mol), and 2-propanol (104.5 g, 1.74 mol) were placed in a reactor, heated at 50 to 55° C., and stirred for 1 hour. Next, the mixture was cooled to 40° C., subjected to addition of sodium borohydride (0.71 g, 0.019 mol), and stirred at 35 to 45° C. for 2 hours. Subsequently, (3Z,6Z)-1-chloro-3,6-nonadiene (comp. of Formula 1) (95.6 g, 0.60 mol) was added into the reactor in which the NiZn catalyst had been prepared, then the mixture was warmed to 40 to 50° C., and hydrogen gas was fed thereto for 21.5 hours while the progress of the reaction was observed. The resulting mixture was cooled to 40° C. or less, and the NiZn catalyst was filtered off, then water (19.9 g) was added to the filtrate for liquid separation. The organic phase was concentrated under reduced pressure, and then the residue was subjected to vacuum distillation to obtain 1-chlorononane (comp. of Formula 2) (88.6 g, 0.54 mol) at a yield of 90.5%.

The yield of nonane, which was a dehalogenation product, was 3.6%, so that the by-product was only slightly yielded.

1-chlorononane (comp. of Formula 2)

[Nuclear magnetic resonance spectrum] $^1$H-NMR (500 MHz, CDCl$_3$): δ=0.88 (3H, t, J=7.1 Hz), 1.21-1.34 (10H, m), 1.38-1.46 (2H, m), 1.76 (2H, quint-like, J=7.2 Hz), 3.53 (2H, t, J=6.7 Hz); $^{13}$C-NMR (125 MHz, CDCl$_3$): δ=14.08, 22.64, 26.88, 28.89, 29.20, 29.42, 31.84, 32.65, 45.17

[Mass spectrum] EI-mass spectrum (70 eV): m/z 162 (M$^+$), 119, 105, 91, 69, 55, 43, 29

[Infrared absorption spectrum] (NaCl): ν=2956, 2926, 2856, 1466, 724, 654

Example 11 <Production of Cl(CH$_2$)$_8$CH$_3$>

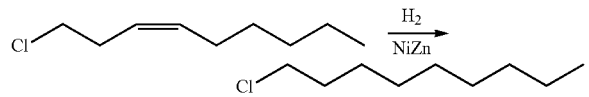

Nickel(II) acetate (1.80 g, 0.0072 mol), zinc(II) oxide (0.59 g, 0.0072 mol), and ethanol (51.5 g, 1.12 mol) were placed in a reactor, heated at 50 to 55° C., and stirred for 1 hour. Next, the mixture was cooled to 40° C., subjected to addition of sodium borohydride (0.35 g, 0.0093 mol), and stirred at 35 to 45° C. for 2 hours. Subsequently, (3Z)-1-chloro-3-nonene (comp. of Formula 1) (95.4 g, 0.59 mol) was added into the reactor in which the NiZn catalyst had been prepared, then the mixture was warmed to 40 to 50° C., and hydrogen gas was fed thereto for 16 hours while the progress of the reaction was observed. The resulting mixture was cooled to 40° C. or less, and the NiZn catalyst was filtered off, then water (19.6 g) was added to the filtrate for liquid separation. The organic phase was concentrated under reduced pressure, and then the residue was subjected to vacuum distillation to obtain 1-chlorononane (comp. of Formula 2) (86.5 g, 0.53 mol) at a yield of 89.6%.

The yield of nonane, which was a dehalogenation product, was 4.6%, so that the by-product was only slightly yielded.

1-chlorononane (comp. of Formula 2)

[Nuclear magnetic resonance spectrum] $^1$H-NMR (500 MHz, CDCl$_3$): δ=0.88 (3H, t, J=7.1 Hz), 1.21-1.34 (10H, m), 1.38-1.46 (2H, m), 1.76 (2H, quint-like, J=7.2 Hz), 3.53 (2H, t, J=6.7 Hz); $^{13}$C-NMR (125 MHz, CDCl$_3$): δ=14.08, 22.64, 26.88, 28.89, 29.20, 29.42, 31.84, 32.65, 45.17

[Mass spectrum] EI-mass spectrum (70 eV): m/z 162 (M$^+$), 119, 105, 91, 69, 55, 43, 29

[Infrared absorption spectrum] (NaCl): ν=2956, 2926, 2856, 1466, 724, 654

Example 12 <Production of Cl(CH$_2$)$_{15}$CH$_3$>

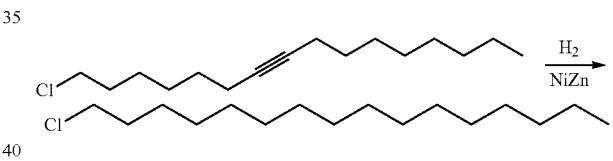

Nickel(II) acetate (1.15 g, 0.0046 mol), zinc(II) oxide (0.38 g, 0.0047 mol), and ethanol (32.8 g, 1.12 mol) were placed in a reactor, heated at 50 to 55° C., and stirred for 1 hour. Next, the mixture was cooled to 40° C., subjected to addition of sodium borohydride (0.22 g, 0.0058 mol), and stirred at 35 to 45° C. for 2 hours. Subsequently, 1-chloro-7-hexadecyne (comp. of Formula 1) (97.1 g, 0.38 mol) was added into the reactor in which the NiZn catalyst had been prepared, then the mixture was warmed to 40 to 50° C., and hydrogen gas was fed thereto for 40.5 hours while the progress of the reaction was observed. The resulting mixture was cooled to 40° C. or less, and the NiZn catalyst was filtered off, then water (12.5 g) was added to the filtrate for liquid separation. The organic phase was concentrated under reduced pressure, and then the residue was subjected to vacuum distillation to obtain 1-chlorohexadecane (comp. of Formula 2) (96.3 g, 0.37 mol) at a yield of 97.7%.

The yield of hexadecane, which was a dehalogenation product, was 2.1%, so that the by-product was only slightly yielded.

1-chlorohexadecane (comp. of Formula 2)

[Nuclear magnetic resonance spectrum] $^1$H-NMR (500 MHz, CDCl$_3$): δ=0.88 (3H, t, J=7.1 Hz), 1.23-1.34 (24H, m), 1.38-1.46 (2H, m), 1.77 (2H, quint-like, J=7.2 Hz), 3.53

(2H, t, J=6.9 Hz); $^{13}$C-NMR (125 MHz, CDCl$_3$): δ=14.11, 22.70, 26.90, 28.91, 29.38, 29.48, 29.56, 29.63, 29.66, 29.69, 31.93, 32.67, 45.17

[Mass spectrum] EI-mass spectrum (70 eV): m/z 260 (M+), 245, 231, 217, 203, 189, 175, 161, 147, 133, 119, 105, 91, 71, 57, 43, 29

[Infrared absorption spectrum] (NaCl): ν=2954, 2924, 2853, 1466, 722, 655

Example 13 <Production of Cl(CH$_2$)$_7$CH$_3$>

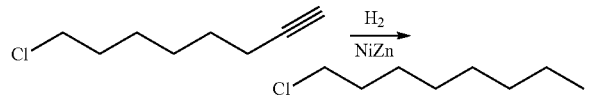

Nickel(II) acetate (2.08 g, 0.0084 mol), zinc(II) oxide (0.68 g, 0.0084 mol), and methanol (59.4 g, 1.85 mol) were placed in a reactor, heated at 50 to 55° C., and stirred for 1 hour. Next, the mixture was cooled to 40° C., subjected to addition of sodium borohydride (0.40 g, 0.011 mol), and stirred at 35 to 45° C. for 2 hours. Subsequently, 1-chloro-7-octyne (comp. of Formula 1) (99.0 g, 0.68 mol) was added into the reactor in which the NiZn catalyst had been prepared, then the mixture was warmed to 40 to 50° C., and hydrogen gas was fed thereto for 11 hours while the progress of the reaction was observed. The resulting mixture was cooled to 40° C. or less, and the NiZn catalyst was filtered off, then water (22.6 g) was added to the filtrate for liquid separation. The organic phase was concentrated under reduced pressure, and then the residue was subjected to vacuum distillation to obtain 1-chlorooctane (comp. of Formula 2) (84.0 g, 0.56 mol) at a yield of 82.5%.

The octane, which was a dehalogenation product, was not yielded as a by-product.

1-chlorooctane (comp. of Formula 2)

[Nuclear magnetic resonance spectrum] $^1$H-NMR (500 MHz, CDCl$_3$): δ=0.88 (3H, t, J=6.9 Hz), 1.23-1.34 (8H, m), 1.38-1.46 (2H, m), 1.77 (2H, quint-like, J=7.2 Hz), 3.53 (2H, t, J=7.1 Hz); $^{13}$C-NMR (125 MHz, CDCl$_3$): δ=14.06, 22.61, 26.88, 28.85, 29.13, 31.75, 32.65, 45.16

[Mass spectrum] EI-mass spectrum (70 eV): m/z 148 (M+), 119, 105, 91, 83, 69, 55, 43, 29

[Infrared absorption spectrum] (NaCl): ν=2957, 2927, 2856, 1466, 725, 654

Example 14 <Production of Cl(CH$_2$)$_9$CH(CH$_3$)CH$_2$CH$_2$CH$_2$CH$_3$>

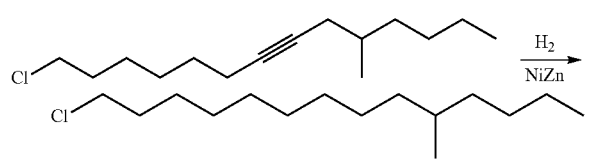

Nickel(II) acetate (2.49 g, 0.010 mol), zinc(II) oxide (0.81 g, 0.010 mol), and ethanol (71.1 g, 1.54 mol) were placed in a reactor, heated at 50 to 55° C., and stirred for 1 hour. Next, the mixture was cooled to 40° C., subjected to addition of sodium borohydride (0.48 g, 0.013 mol), and stirred at 35 to 45° C. for 2 hours. Subsequently, 1-chloro-10-methyl-7-tetradecyne (comp. of Formula 1) (99.5 g, 0.41 mol) was added into the reactor in which the NiZn catalyst had been prepared, then the mixture was warmed to 40 to 50° C., and hydrogen gas was fed thereto for 53 hours while the progress of the reaction was observed. The resulting mixture was cooled to 40° C. or less, and the NiZn catalyst was filtered off, then water (13.5 g) was added to the filtrate for liquid separation. The organic phase was concentrated under reduced pressure, and then the residue was subjected to vacuum distillation to obtain 1-chloro-10-methyltetradecane (comp. of Formula 2) (93.3 g, 0.38 mol) at a yield of 92.2%.

The yield of 10-methyltetradecane, which was a dehalogenation product, was 0.17%, so that almost no by-product was yielded.

1-chloro-10-methyltetradecane (comp. of Formula 2)

[Nuclear magnetic resonance spectrum] $^1$H-NMR (500 MHz, CDCl$_3$): δ=0.84 (3H, d, J=6.5 Hz), 0.89 (3H, t, J=7.1 Hz), 1.04-1.13 (2H, m), 1.18-1.33 (16H, m), 1.38-1.46 (2H, m), 1.77 (2H, quint-like, J=7.2 Hz), 3.53 (2H, t, J=6.9 Hz); $^{13}$C-NMR (125 MHz, CDCl$_3$): δ=14.17, 19.70, 23.05, 26.90, 27.06, 28.91, 29.34, 29.48, 29.59, 29.97, 32.66, 32.72, 36.78, 37.07, 45.18

[Mass spectrum] EI-mass spectrum (70 eV): m/z 246 (M+), 231, 188, 160, 147, 133, 119, 97, 85, 71, 57, 43, 29

[Infrared absorption spectrum] (NaCl): ν=2955, 2925, 2855, 1465, 728,

Example 15 <Production of CH$_3$CHCl(CH$_2$)$_8$CH$_3$>

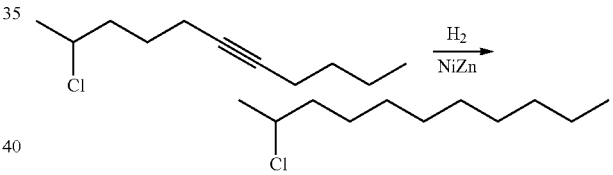

Nickel(II) acetate (1.12 g, 0.0045 mol), zinc(II) oxide (0.37 g, 0.0045 mol), and ethanol (32.2 g, 0.70 mol) were placed in a reactor, heated at 50 to 55° C., and stirred for 1 hour. Next, the mixture was cooled to 40° C., subjected to addition of sodium borohydride (0.22 g, 0.0058 mol), and stirred at 35 to 45° C. for 2 hours. Subsequently, 2-chloro-6-undecyne (comp. of Formula 1) (69.4 g, 0.37 mol) was added into the reactor in which the NiZn catalyst had been prepared, then the mixture was warmed to 40 to 50° C., and hydrogen gas was fed thereto for 12.5 hours while the progress of the reaction was observed. The resulting mixture was cooled to 40° C. or less, and the NiZn catalyst was filtered off, then water (12.4 g) was added to the filtrate for liquid separation. The organic phase was concentrated under reduced pressure, and then the residue was subjected to vacuum distillation to obtain 2-chloroundecane (comp. of Formula 2) (62.5 g, 0.33 mol) at a yield of 88.2%.

The yield of undecane, which was a dehalogenation product, was 0.53%, so that almost no by-product was yielded.

2-chloroundecane (comp. of Formula 2)

[Nuclear magnetic resonance spectrum] $^1$H-NMR (500 MHz, CDCl$_3$): δ=0.88 (3H, t, J=7.1 Hz), 1.22-1.34 (12H, m), 1.33-1.52 (2H, m), 1.50 (3H, d, J=6.5 Hz), 1.62-1.76 (2H, m), 4.02 (1H, sext-like, J=6.6 Hz); $^{13}$C-NMR (125 MHz, CDCl$_3$): δ=14.09, 22.67, 25.34, 26.67, 29.12, 29.29, 29.50, 29.52, 31.87, 40.37, 58.95

[Mass spectrum] EI-mass spectrum (70 eV): m/z 190 (M+), 154, 125, 111, 97, 83, 69, 55, 43, 29

[Infrared absorption spectrum] (NaCl): ν=2956, 2926, 2855, 1465, 722, 615

Example 16 <Production of Br(CH$_2$)$_9$CH$_3$>

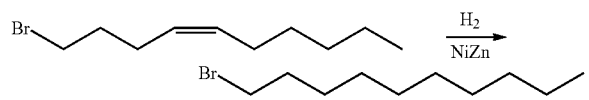

Nickel(II) acetate (1.34 g, 0.0054 mol), zinc(II) oxide (0.44 g, 0.0054 mol), and 2-propanol (38.3 g, 0.64 mol) were placed in a reactor, heated at 50 to 55° C., and stirred for 1 hour. Next, the mixture was cooled to 40° C., subjected to addition of sodium borohydride (0.26 g, 0.0069 mol), and stirred at 35 to 45° C. for 2 hours. Subsequently, (4Z)-1-bromo-4-decene (comp. of Formula 1) (96.9 g, 0.44 mol) was added into the reactor in which the NiZn catalyst had been prepared, then the mixture was warmed to 40 to 50° C., and hydrogen gas was fed thereto for 6 hours while the progress of the reaction was observed. The resulting mixture was cooled to 40° C. or less, and the NiZn catalyst was filtered off, then water (14.6 g) was added to the filtrate for liquid separation. The organic phase was concentrated under reduced pressure, and then the residue was subjected to vacuum distillation to obtain 1-bromodecane (comp. of Formula 2) (93.4 g, 0.42 mol) at a yield of 95.5%.

The yield of decane, which was a dehalogenation product, was 3.0%, so that the by-product was only slightly yielded.

1-bromodecane (comp. of Formula 2)

[Nuclear magnetic resonance spectrum] $^1$H-NMR (500 MHz, CDCl$_3$): δ=0.88 (3H, t, J=7.1 Hz), 1.22-1.34 (12H, m), 1.38-1.45 (2H, m), 1.85 (2H, quint-like, J=7.3 Hz), 3.40 (2H, t, J=6.9 Hz); $^{13}$C-NMR (125 MHz, CDCl$_3$): δ=14.10, 22.67, 28.17, 28.76, 29.28, 29.44, 29.50, 31.86, 32.84, 34.05

[Mass spectrum] EI-mass spectrum (70 eV): m/z 220 (M+), 149, 135, 121, 99, 85, 69, 57, 43, 29

[Infrared absorption spectrum] (NaCl): ν=2957, 2925, 2854, 1465, 647, 564

Example 17 <Production of Cl(CH$_2$)$_8$Si(CH$_3$)$_3$>

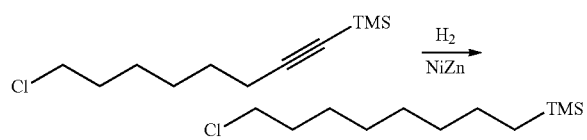

Nickel(II) acetate (1.39 g, 0.0056 mol), zinc(II) oxide (0.45 g, 0.0055 mol), and ethanol (39.7 g, 0.86 mol) were placed in a reactor, heated at 50 to 55° C., and stirred for 1 hour. Next, the mixture was cooled to 40° C., subjected to addition of sodium borohydride (0.27 g, 0.0071 mol), and stirred at 35 to 45° C. for 2 hours. Subsequently, 1-trimethylsilyl-8-chloro-1-octyne (comp. of Formula 1) (99.2 g, 0.46 mol) was added into the reactor in which the NiZn catalyst had been prepared, then the mixture was warmed to 40 to 50° C., and hydrogen gas was fed thereto for 28.5 hours while the progress of the reaction was observed. The resulting mixture was cooled to 40° C. or less, and the NiZn catalyst was filtered off, then water (16.4 g) was added to the filtrate for liquid separation. The organic layer was concentrated under reduced pressure, and then the residue was subjected to vacuum distillation to obtain 1-trimethylsilyl-8-chloro-octane (comp. of Formula 2) (89.4 g, 0.40 mol) at a yield of 88.5%.

The 1-chlorooctane was produced at a yield 6.9% as a by-product by desilylation, but neither 1-trimethylsilyloctane nor octane was yielded as a by-product by dehalogenation.

1-trimethylsilyl-8-chloro-octane (comp. of Formula 2)

[Nuclear magnetic resonance spectrum] $^1$H-NMR (500 MHz, CDCl$_3$): δ=-0.031 (9H, s), 0.47 (2H, t-like, J=7.8 Hz), 1.25-1.33 (8H, m), 1.38-1.46 (2H, m), 1.77 (2H, quint-like, J=7.2 Hz), 3.53 (2H, t, J=6.9 Hz); $^{13}$C-NMR (125 MHz, CDCl$_3$): δ=-1.65, 16.66, 23.86, 26.91, 28.83, 29.17, 32.65, 33.48, 45.17

[Mass spectrum] EI-mass spectrum (70 eV): m/z 220 (M+), 205, 93, 73, 56, 43, 29

[Infrared absorption spectrum] (NaCl): ν=2953, 2923, 2854, 1464, 1247, 862, 836, 725, 655

Example 18 <Production of Cl(CH$_2$)$_{10}$OH>

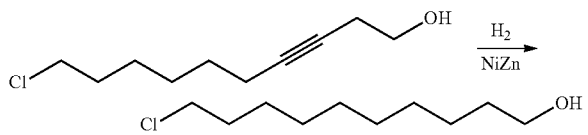

Nickel(II) acetate (84.6 g, 0.34 mol), zinc(II) oxide (27.7 g, 0.34 mol), and 2-propanol (2,414.6 g, 40.18 mol) were placed in a reactor, heated at 50 to 55° C., and stirred for 1 hour. Next, the mixture was cooled to 40° C., subjected to addition of sodium borohydride (16.5 g, 0.44 mol), and stirred at 35 to 45° C. for 2 hours to obtain a NiZn catalyst. The mixture was cooled to 30° C. or less, and the thus-obtained NiZn catalyst (47.6 g) and 1-hydroxy-10-chloro-3-decyne (comp. of Formula 1) (98.3 g, 0.52 mol) were placed in another reactor, and the mixture was warmed to 40 to 50° C., then hydrogen gas was fed thereto for 7 hours. The mixture was cooled to 40° C. or less, and the catalyst was filtered off, then water (18.7 g) was added to the filtrate for liquid separation. The organic phase was concentrated under reduced pressure, and then the residue was subjected to vacuum distillation to obtain 1-hydroxy-10-chlorodecane (comp. of Formula 2) (97.2 g, 0.50 mol) at a yield of 96.8%.

The 1-decanol was not yielded as a by-product by dehalogenation.

1-hydroxy-10-chlorodecane (comp. of Formula 2)

[Nuclear magnetic resonance spectrum] $^1$H-NMR (500 MHz, CDCl$_3$): δ=1.25-1.36 (10H, m), 1.36-1.44 (2H, m), 1.55 (2H, quint-like, J=7.1 Hz), 1.58 (1H, br. s), 1.75 (quint-like, J=7.2 Hz), 3.52 (2H, t, J=6.9 Hz), 3.62 (2H, t, J=6.7 Hz); $^{13}$C-NMR (125 MHz, CDCl$_3$): δ=25.66, 26.81, 28.80, 29.33, 29.42, 32.57, 32.70, 45.13, 62.95

[Mass spectrum] EI-mass spectrum (70 eV): m/z 193 (M+), 174, 146, 132, 118, 104, 83, 69, 55, 41, 29

[Infrared absorption spectrum] (NaCl): ν=3334, 2928, 2855, 1465, 1057, 723, 652

Example 19 <Production of Cl(CH$_2$)$_2$CH(CH$_3$)(CH$_2$)$_3$CH(CH$_3$)$_2$>

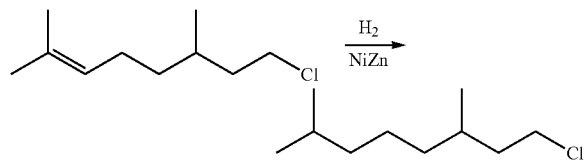

Nickel(II) acetate (84.6 g, 0.34 mol), zinc(II) oxide (27.7 g, 0.34 mol), and ethanol (2,414.6 g, 52.41 mol) were placed in a reactor, heated at 50 to 55° C., and stirred for 1 hour. Next, the mixture was cooled to 40° C., subjected to addition of sodium borohydride (16.5 g, 0.44 mol), and stirred at 35 to 45° C. for 2 hours to obtain a NiZn catalyst. The mixture was cooled to 30° C. or less, and the thus-obtained NiZn catalyst (150.4 g) and 8-chloro-2,6-dimethyl-2-octene (comp. of Formula 1) (95.86 g, 0.55 mol) were placed in another reactor, and the mixture was warmed to 45 to 55° C., then hydrogen gas was fed thereto for 61 hours. The mixture was cooled to 40° C. or less, and the catalyst was filtered off, then water (16.6 g) was added to the filtrate for liquid separation. The organic phase was concentrated under reduced pressure, and then the residue was subjected to vacuum distillation to obtain 1-chloro-3,7-dimethyloctane (comp. of Formula 2) (92.6 g, 0.52 mol) at a yield of 95.5%.

The yield of 2,6-dimethyloctane, which was a dehalogenation product, was 0.29%, so that almost no by-product was yielded.

1-chloro-3,7-dimethyloctane (comp. of Formula 2)

[Nuclear magnetic resonance spectrum] $^1$H-NMR (500 MHz, CDCl$_3$): δ=0.868 (3H, d, J=6.5 Hz), 0.869 (3H, d, J=6.5 Hz), 0.89 (3H, d, J=6.5 Hz), 1.07-1.17 (3H, m), 1.21-1.38 (3H, m), 1.46-1.61 (2H, m), 1.61-1.69 (1H, m), 1.75-1.83 (1H, m), 3.50-3.62 (1H, m); $^{13}$C-NMR (125 MHz, CDCl$_3$): δ=19.05, 22.56, 22.67, 24.55, 27.93, 30.36, 36.82, 39.15, 39.78, 43.36

[Mass spectrum] EI-mass spectrum (70 eV): m/z 176 (M+), 133, 113, 97, 83, 71, 57, 43, 29

[Infrared absorption spectrum] (NaCl): ν=2956, 2928, 2870, 1466, 1382, 1366, 727, 659

Example 20 <Production of Cl(CH$_2$)$_7$CH$_3$>

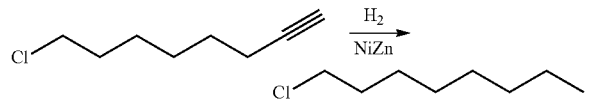

Nickel(II) chloride (23.8 g, 0.18 mol), zinc(II) oxide (14.9 g, 0.18 mol), and ethanol (1,301.8 g, 28.26 mol) were placed in a reactor, heated at 50 to 55° C., and stirred for 1 hour. Next, the mixture was cooled to 40° C., subjected to addition of sodium borohydride (8.88 g, 0.23 mol), and stirred at 35 to 45° C. for 2 hours to obtain a NiZn catalyst. The mixture was cooled to 30° C. or less, and the thus-obtained NiZn catalyst (62.4 g) and 1-chloro-7-octyne (comp. of Formula 1) (99.0 g, 0.68 mol) were placed in another reactor, and the mixture was warmed to 40 to 50° C., then hydrogen gas was fed thereto for 7 hours while the progress of the reaction was observed. The resulting mixture was cooled to 40° C. or less, and the NiZn catalyst was filtered off, then water (22.6 g) was added to the filtrate for liquid separation. The organic phase was concentrated under reduced pressure, and then the residue was subjected to vacuum distillation to obtain 1-chlorooctane (comp. of Formula 2) (82.5 g, 0.56 mol) at a yield of 81.3%.

The octane was not yielded as a by-product by dehalogenation.

1-chlorooctane (comp. of Formula 2)

[Nuclear magnetic resonance spectrum] $^1$H-NMR (500 MHz, CDCl$_3$): δ=0.88 (3H, t, J=6.9 Hz), 1.23-1.34 (8H, m), 1.38-1.46 (2H, m), 1.77 (2H, quint-like, J=7.2 Hz), 3.53 (2H, t, J=7.1 Hz); $^{13}$C-NMR (125 MHz, CDCl$_3$): δ=14.06, 22.61, 26.88, 28.85, 29.13, 31.75, 32.65, 45.16

[Mass spectrum] EI-mass spectrum (70 eV): m/z 148 (M+), 119, 105, 91, 83, 69, 55, 43, 29

[Infrared absorption spectrum] (NaCl): ν=2957, 2927, 2856, 1466, 725, 654

It is evident from results of Examples 1 to 20 that the NiZn catalyst suppressed dehalogenation and enabled the efficient production of halide compounds.

When 8-chloro-1,1-diethoxy-2-octyne in Example 2 and 7-chloro-1,1-diethoxy-2-heptyne in Example 3 were reduced, the yields of the reduced halide compounds were 95.0% or more, while the yields of by-products by dehalogenation were less than 1.0%. Thus, these results are satisfactory.

In particular, when 6-chloro-1,1-diethoxy-2-hexyne in Example 1, 9-chloro-1,1-diethoxy-2-nonyne in Example 4, 1-hydroxy-10-chloro-3-decyne in Example 18, and 8-chloro-2,6-dimethyl-2-octene in Example 19 were reduced, the yields of the reduced halide compounds were 95.0% or more, while the yields of by-products by dehalogenation were less than 0.5%. Thus, these results are satisfactory.

The invention claimed is:

1. A method for producing a reduced halide compound, comprising steps of:
   reacting a nickel compound, a zinc compound, and a borohydride compound in a solvent to obtain a reduction catalyst; and
   subjecting a halide compound having one or more carbon-carbon unsaturated bonds to catalytic reduction in the presence of the reduction catalyst to reduce at least one of the one or more carbon-carbon unsaturated bonds to thereby obtain a reduced halide compound.

2. The method for producing a halide compound according to claim 1, wherein the halide compound having one or more carbon-carbon unsaturated bonds is denoted by General Formula (1):

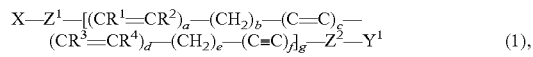

wherein

X is a halogen atom;

$R^1$, $R^2$, $R^3$, and $R^4$ are each independently a hydrogen atom, a halogen atom, a monovalent hydrocarbon group having 1 to 18 carbon atoms, or an acyl group having 1 to 18 carbon atoms beside a carbon atom of a carbonyl group, or are bonded together to form a divalent hydrocarbon group, $R^1$-$R^2$, $R^1$-$R^3$, $R^1$-$R^4$, $R^2$-$R^3$, $R^2$-$R^4$ or $R^3$-$R^4$, having 1 to 18 carbon atoms;

$Z^1$ and $Z^2$ are each independently a divalent hydrocarbon group having 1 to 18 carbon atoms, or a single bond;

$Y^1$ is a hydrogen atom, a halogen atom, a protected formyl group, a hydroxy group, an acyl group, an acyloxy group, an alkoxy group, an alkoxyalkoxy group, a carboxyl group, an amino group, an amino group monosubstituted with a monovalent hydrocarbon group having 1 to 18 carbon atoms, an amino group disubstituted with two monovalent hydrocarbon groups each having 1 to 18 carbon atoms, an acylamino group, a silyl group, or an alkoxycarbonyloxy group; and a, b, c, d, e and f are each an integer of 0 to 8 with the proviso that not all of a, c, d and f are 0, and g is an integer of 1 to 8; and the reduced halide compound in which at least one of the one or more carbon-carbon unsaturated bonds is reduced is denoted by General Formula (2):

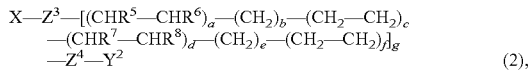

(2), wherein

X is a halogen atom;

$R^5$, $R^6$, $R^7$, and $R^8$ are each independently a hydrogen atom, a halogen atom, a monovalent hydrocarbon group having 1 to 18 carbon atoms, or an acyl group having 1 to 18 carbon atoms beside a carbon atom of a carbonyl group, or are bonded together to form a divalent hydrocarbon group, $R^5$-$R^6$, $R^5$-$R^1$, $R^5$-$R^8$, $R^6$-$R^7$, $R^6$-$R^8$ or $R^7$-$R^8$, having 1 to 18 carbon atoms;

$Z^3$ and $Z^4$ are each independently a divalent hydrocarbon group having 1 to 18 carbon atoms, or a single bond;

$Y^2$ is a hydrogen atom, a halogen atom, a protected formyl group, a hydroxy group, an acyl group, an acyloxy group, an alkoxy group, an alkoxyalkoxy group, a carboxyl group, an amino group, an amino group monosubstituted with a monovalent hydrocarbon group having 1 to 18 carbon atoms, an amino group disubstituted with two monovalent hydrocarbon groups each having 1 to 18 carbon atoms, an acylamino group, a silyl group, or an alkoxycarbonyloxy group; and a, b, c, d, e and f are each an integer of 0 to 8 with the proviso that not all of a, c, d and f are 0, and g is an integer of 1 to 8.

3. The method for producing a reduced halide compound according to claim 1, wherein the solvent is an alcohol.

4. The method for producing a reduced halide compound according to claim 1, wherein the nickel compound is a nickelous compound.

5. The method for producing a reduced halide compound according to claim 1, wherein the zinc compound is a divalent zinc compound.

6. The method for producing a reduced halide compound according to claim 1, wherein the borohydride compound is an alkali metal borohydride.

7. The method for producing a reduced halide compound according to claim 1, wherein the protected formyl group is protected by a protective group to form O,O-acetal denoted by General Formula (3):

(3), wherein $R^9$ and $R^{10}$ are each independently a monovalent hydrocarbon group having 1 to 18 carbon atoms or are bonded together to form a divalent hydrocarbon group, $R^9$-$R^{10}$, having 1 to 18 carbon atoms.

\* \* \* \* \*

UNITED STATES PATENT AND TRADEMARK OFFICE
CERTIFICATE OF CORRECTION

PATENT NO. : 10,676,417 B2
APPLICATION NO. : 16/388309
DATED : June 9, 2020
INVENTOR(S) : Miyake et al.

It is certified that error appears in the above-identified patent and that said Letters Patent is hereby corrected as shown below:

On the Title Page

Item (56) References Cited, OTHER PUBLICATIONS, Column 2, Line 26, Van et al. cite:
Please correct "Van" to read -- Yan --

Item (56) References Cited, OTHER PUBLICATIONS, Column 2, Line 29, Acosta et al. cite:
Please correct "Ttansition" to read -- Transition --

In the Specification

Column 22, Line 30:
Please correct "728," to read -- 728, 655 --

In the Claims

Column 26, Line 66, Claim 2, General Formula (1):
Please correct "$(C=C)_c$" to read -- $(C\equiv C)_c$ --

Column 26, Line 67, Claim 2, General Formula (1):
Please correct "$(C\equiv C)_f$" to read -- $(C\equiv C)_f$ --

Column 27, Line 23, Claim 2:
Please correct "fare" to read -- f are --

Column 28, Line 1, Claim 2:
Please correct "$R^5$-$R^1$" to read -- $R^5$-$R^7$ --

Column 28, Line 15, Claim 2:
Please correct "fare" to read -- f are --

Signed and Sealed this
Twentieth Day of October, 2020

Andrei Iancu
*Director of the United States Patent and Trademark Office*